(12) United States Patent
Xiao et al.

(10) Patent No.: US 7,943,092 B2
(45) Date of Patent: May 17, 2011

(54) PORTABLE SURFACE PLASMON RESONANCE BIOSENSOR

(75) Inventors: Caide Xiao, Rochester, MI (US); Xiangqun Zeng, Rochester, MI (US)

(73) Assignee: Oakland University, Rochester, MI (US)

( * ) Notice: Subject to any disclaimer, the term of this patent is extended or adjusted under 35 U.S.C. 154(b) by 1118 days.

(21) Appl. No.: 11/581,260

(22) Filed: Oct. 10, 2006

(65) Prior Publication Data

US 2010/0248283 A1 Sep. 30, 2010

(51) Int. Cl.
*G01N 21/00* (2006.01)
*G01N 21/76* (2006.01)
*C12M 1/34* (2006.01)
*C12M 3/00* (2006.01)

(52) U.S. Cl. .......... 422/82.11; 422/82.05; 436/172; 435/288.7

(58) Field of Classification Search .......... 422/82.11, 422/82.05; 436/172
See application file for complete search history.

(56) References Cited

U.S. PATENT DOCUMENTS

| | | | |
|---|---|---|---|
| 2,996,616 A * | 8/1961 | Heinz et al. | 378/74 |
| 5,313,264 A * | 5/1994 | Ivarsson et al. | 356/73 |
| 6,127,624 A * | 10/2000 | Ishida et al. | 136/257 |
| 6,194,223 B1 * | 2/2001 | Herrmann et al. | 436/518 |
| 6,493,097 B1 | 12/2002 | Ivarsson et al. | |
| 6,714,303 B2 | 3/2004 | Ivarsson et al. | |
| 7,084,980 B2 | 8/2006 | Jones et al. | |
| 2005/0003560 A1 | 1/2005 | Zeng et al. | |

OTHER PUBLICATIONS

Bailey, Larry E. et al., "Using Surface Plasmon Resonance and the Quartz Crystal Microbalance to Monitor in Situ the Interfacial Behavior of Thin Organic Films," Langmuir 2002, 18, p. 479-489.*
Kretschmann, E. (1971) "Die Bestimmung optischer Konstanten von Matellen durch Anregung von oberflachenplsama-schwingungen." Z. Phys., 241: 313-324.
Liedberg, B. et al., (1983). "Surface Plasmon Resonance for Gas Detection and Biosensing" Sensors and Actuators, 4: 299-304.
Liedberg, B. et al., (1995) "Biosensing with surface plasmon resonance—how it all started.", Biosensors and Bioelectronics 10(8): i-ix.
Caide, X. and F. Sui Sen (1999), "Numerical simulations of surface plasmon resonance system for monitoring DNA hybridization and detecting protein-lipid film interactions," European Biophysics Journal 28(2): 151-157.
Rothenhausler, B. and W. Knoll, Surface plasmon microscopy. Nature, 1988, 332: p. 615-617.
Zhou, Y., X. Caide, and S.F. Sui, Assembly of supported membranes studied by surface plasmon microscopy. Molecular Crystals and Liquid Crystals Science and Technology Section A Molecular Crystals and Liquid Crystals, 1999: 337: p. 61-64.
Mohammad, I. et al., "Is biosensor a viable method for food allergen detection?" Analytica Chimica Acta 444 (2001) 97-102.

* cited by examiner

*Primary Examiner* — Sam P Siefke
*Assistant Examiner* — Bryan T Kilpatrick
(74) *Attorney, Agent, or Firm* — Ian C. McLeod; Steven M. Parks

(57) ABSTRACT

A surface plasmon resonance biosensor device and system are provided. The simplicity of SPR biosensor design allows easy integration with both QCM and electrochemistry techniques, not found in current SPR biosensor devices. In some embodiments, the surface plasmon resonance biosensor device has a dual SPR/QCM sample holder which allows simultaneous detection by both surface plasmon resonance and also quartz crystal microbalance (QCM) techniques. In additional embodiments, the surface plasmon resonance biosensor device and/or the dual SPR/QCM technique can be integrated with electrochemistry techniques by incorporate reference and counter electrodes in the SPR or SPR/QCM sample holder. Methods of using the device and system to determine whether an analyte of interest is present in a sample are also provided.

24 Claims, 22 Drawing Sheets

PORTABLE SURFACE PLASMON RESONANCE BIOSENSOR

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION (1) Field of the Invention

The present invention relates generally to surface plasmon resonance. Specifically, the present invention relates to a simple and reliable surface plasmon resonance biosensor device.

(2) Description of the Related Art

Life phenomena are results of biomolecular interactions. Biomolecular interactions are traditionally studied using techniques such as enzyme-linked immunosorbent assay (ELISA), radioimmunoassay (RIA), and affinity chromatography. Surface plasmon resonance (SPR) biosensing technique provides two main advantages over these techniques. First, the biomolecular interactions can be monitored in real-time. Second, it is not necessary to label the interacting biomolecules. Surface plasmon is a quantum name for an electric charge density wave that propagates on an interface between a metal and a dielectric, just like photon is a quantum name for a light wave. Surface plasmons are described in U.S. Pat. No. 7,084,980 to Jones, et al. hereby incorporated herein by reference in its entirety. Surface plasmons resonate upon excitation by electromagnetic radiation entering an interface of metallic material and a dielectric material. The surface plasmon responds to changes in the environment in close proximity to the interface. This fact makes surface plasmon resonance useful for the detection of biomolecular interactions. A practical and commonly used method by which to excite the surface plasmon was initially suggested by Kretschmann (Kretschmann, E. (1971) "Die Bestimmung optischer Konstanten von Metallen durch Anregung von Oberflächen-plasma-schwingungen." Z. Phys., 241: 313-324). In the Kretschmann configuration, a prism is used as a coupler between incident photons and surface plasmons on a surface of a thin metal film evaporated onto the prism. Since the refractive index of a prism is usually higher than the refractive index of its ambient environment (air or water), there is a critic incident angle $\theta_c$ for the light reflected inside the prism. Under the conditions when $\theta \geq \theta_c$, total light reflection occurs inside the prism. For p-polarized light, the incident photons can excite surface plasmons on surface of a metal film. The incident angle for surface plasmon resonance is called resonance angle ($\theta_{SPR}$). Since there is energy transfer from photons to surface plasmons during resonance, the reflectivity of incident light could change from 1 to 0 at $\theta_{SPR}$. A graph of the relationship between reflectivity and incident angle is called an SPR spectrum.

Under some conditions, the shift of the resonance angle $\Delta\theta_{SPR}$ is proportional to $(n_s-n_a)l$, where $n_s$ and $l$ are sample refractive index and thickness, $n_a$ is the ambient refractive index. From the linear relationship, the amount of protein adsorbed on a gold film can be detected at as low as 0.01 ng/mm², and the affinity of ligand-receptor interaction can be detected. After Nylander (Nylander, C., Liedberg, B. & Lind, T. (1982/83), "Gas detection by means of surface plasmon resonance" Sensors and Actuators, 3: 79-88) published the first paper about SPR biosensing in 1983, a project was initiated at Pharmacia of Sweden (Liedberg, B., C. Nylander, et al. (1995). "Biosensing with surface plasmon resonance—how it all started", Biosensors and Bioelectronics 10(8): i-ix.) in 1984. In 1986 a separate company, Pharmacia Biosensor, was formed for the development of the new biosensor technology. Today the successful Pharmacia Biosensor Company is called Biacore (http://www.biacore.com) and it makes many kinds of commercial SPR biosensors. For biologists, these Biacore SPR biosensors are very useful, but also very expensive. The price of the latest model Biacore 3000 is presently about three hundred thousand dollars and the price of a disposable sensing chip is about one hundred and twenty dollars. A fully used Biacore SPR biosensor can consume thousands of the sensing chips per year.

U.S. Pat. Nos. 6,493,097 and 6,714,303 to Ivarsson et al. teach an apparatus and method of examining thin layer structures on a sensor surface by imaging light reflected by the surface during SPR microscopy. The apparatus uses a light source which illuminate collimator optics to produce a parallel light beam. The light beam passes an interference filter as a monochromatic beam and impinges on two flat scanner mirrors before the light beam is deflected into a prism or grating to the sensor surface. An optical system then produces an image of the sensor surface at a detector. The optical system adds cost and complexity to the apparatus.

While the related art teach surface plasmon resonance biosensors, there still exists a need for an inexpensive and portable surface plasmon resonance biosensor.

OBJECTS

Therefore, it is an object of the present invention to provide an inexpensive and portable surface plasmon resonance biosensor device. These and other objects will become increasingly apparent by reference to the following description.

SUMMARY OF THE INVENTION

The present invention provides a surface plasmon resonance biosensor device for analysis of a fluid sample comprising: a support means; a capacitive angle sensor mounted to the support means having a shaft; a rotatable adapter means rotatably mounted on the shaft; a prism or a half cylinder mounted on the rotatable adapter means; a light source mounted to the support means, positioned to project a beam of light through a first side of the prism or half cylinder to a second side of the prism or half cylinder; a thin metallic film with an inner surface affixed on or adjacent to the prism or half cylinder; a sample holder having a sealing means removably sealed against an exposed surface of the thin metallic film, the sample holder, sealing means and thin metallic film defining a sample chamber; a light response element as a transducer to generate an intensity output mounted on a third side of the prism or half cylinder, wherein when the sample is provided to the sample chamber and the light source projects the beam of light, the capacitive angle sensor measures an incident angle of the beam of light upon the metallic film to provide an incident angle output and the light response element measures light intensity reflected from the inner surface of the thin metallic film to provide the intensity output.

In further embodiments, the metallic film is gold. In still further embodiments, the prism or half cylinder is made of glass or plastic. In still further embodiments, the light response element is a solar cell. In still further embodiments, the light source is a laser apparatus. In still further embodiments, the rotatable adapter means is a rotatable plate. In still further embodiments, the sealing means is an o-ring. In still further embodiments, the support means is a mounting table. In still further embodiments, the surface plasmon resonance biosensor device further comprises a low speed motor rotatably engaged with the rotatable adapter means to turn the rotatable adapter means during analysis of the fluid sample. In still further embodiments, the metallic film is provided upon a transparent cover. In still further embodiments, the sample holder is a dual SPR/QCM sample holder which allows simultaneous detection by both surface plasmon resonance and also quartz crystal microbalance (QCM) techniques.

The present invention provides a surface plasmon resonance biosensor system for analysis of a fluid sample comprising: a support means; a capacitive angle sensor mounted to the support means having a shaft; a rotatable adapter means rotatably mounted on the shaft; a prism or a half cylinder mounted on the rotatable adapter means; a light source mounted to the support means, positioned to project a beam of light through a first side of the prism or half cylinder to a second side of the prism or half cylinder; a thin metallic film with an inner surface affixed on or adjacent to the prism or half cylinder; a sample holder having a sealing means removably sealed against an exposed surface of the thin metallic film, the sample holder, sealing means and thin metallic film defining a sample chamber; a light response element as a transducer to generate an intensity output mounted on a third side of the prism or half cylinder, wherein when the sample is provided to the sample chamber and the light source projects the beam of light, the capacitive angle sensor measures an incident angle of the beam of light upon the metallic film to provide an incident angle output and the light response element measures light intensity reflected from the inner surface of the thin metallic film to provide the intensity output; an analog to digital (A/D) data acquisition device electrically connected to the capacitive angle sensor and the light response element for generating a data signal when the sample is provided to the sample chamber from an incident angle output of the capacitive angle sensor and an intensity output from the light response element; and a personal computer electrically connected to the data acquisition device to receive and process the data signal generated by the data acquisition device and provide a surface plasmon resonance spectrum when the fluid sample is provided to the sample chamber.

In further embodiments, the metallic film is gold. The surface plasmon resonance biosensor device of Claim 12, wherein the metallic film is gold. In still further embodiments, the prism or half cylinder is made of glass or plastic. In still further embodiments, the light response element is a solar cell. In still further embodiments, the light source is a laser apparatus. In still further embodiments, the rotatable adapter means is a rotatable plate. In still further embodiments, the sealing means is an o-ring. In still further embodiments, the support means is a mounting table. In still further embodiments, the surface plasmon resonance biosensor further comprises a low speed motor rotatably engaged with the rotatable plate to turn the plate during analysis of the sample. In still further embodiments, the sample holder is a dual SPR/QCM sample holder which allows simultaneous detection by both surface plasmon resonance and also quartz crystal microbalance (QCM) techniques.

The present invention provides a method to determine whether an analyte of interest is present in a fluid sample comprising: providing a surface plasmon resonance biosensor device comprising a support means; a capacitive angle sensor mounted to the support means having a shaft; a rotatable adapter means rotatably mounted on the shaft; a prism or a half cylinder mounted on the rotatable adapter means; a light source mounted to the support means, positioned to project a beam of light through a first side of the prism or half cylinder to a second side of the prism or half cylinder; a thin metallic film with an inner surface affixed on or adjacent to the prism or half cylinder; a sample holder having a sealing means removably sealed against an exposed surface of the thin metallic film, the sample holder, sealing means and thin metallic film defining a sample chamber; a light response element as a transducer to generate an intensity output mounted on a third side of the prism or half cylinder, wherein when the sample is provided to the sample chamber and the light source projects the beam of light, the capacitive angle sensor measures an incident angle of the beam of light upon the metallic film to provide an incident angle output and the light response element measures light intensity reflected from the inner surface of the thin metallic film to provide the intensity output; providing the fluid sample to the sample chamber; turning the rotatable adapter means; detecting the reflected light intensity with the light response element to provide the intensity output; detecting the incident angle with the capacitive angle sensor to provide the incident angle output; processing the intensity output and the incident angle output to provide an surface plasmon resonance spectrum; analyzing the peak of the surface plasmon resonance spectrum to determine whether the analyte is present in the sample.

In further embodiments, the sample holder is a dual SPR/QCM sample holder, further comprising the steps of analyzing signals from a reference electrode and a counter electrode on the dual SPR/QCM sample holder for electric deposition of polymers and sample reduce/oxidation.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The term "beam of light" as used herein refers to light such as, but not limited to, a beam of laser light.

The term "capture reagent" as used herein refers to any molecule bound to the metallic film that is used to bind an analyte of interest.

The term "prism" or "half cylinder" as used herein refers to any optical material (glass or plastic) having a refractive index above 1.5 with multi-side or a half cylinder geometric shapes. The present examples are directed to a triangular prism, however the term "prism" is not limited to a triangular prism.

The term "light response element" as used herein refers to any light transduction apparatus that can detect light and generate an output in response to the light intensity. Any means for transducing light known in the art, such as, but not limited to a solar cell is encompassed by the term.

The term "light source" as used herein refers to an apparatus for generating monochromatic light such as, but not limited to, a laser apparatus.

The term "rotatable adapter means" as used herein refers to any apparatus for mounting the prism to the capacitive angle sensor of the surface plasmon resonance device. The term "rotatable adapter means" can include an means for adapting such as, but not limited to, a rotatable plate.

The term "sealing means" as used herein refers to any means for sealing known in the art, such as, but not limited to an o-ring or gasket.

The term "SPR" as used herein refers to surface plasmon resonance.

The term "support means" as used herein refers to any apparatus for supporting components of the surface plasmon resonance device such as, but not limited to, a mounting table, surface, stand or other holder known in the art.

The improved portable and economic SPR biosensor of the present invention is a significant improvement of the SPR biosensor that inventor Dr. Xiao Caide described in his Ph.D. thesis work (Caide, X. and F. Sui Sen (1999), "Numerical simulations of surface plasmon resonance system for monitoring DNA hybridization and detecting protein-lipid film interactions," *European Biophysics Journal* 28(2): 151-157.) in China between 1990 and 1996. The improved SPR biosensor of the present invention can be used both for research and educational purposes.

Figure 1:
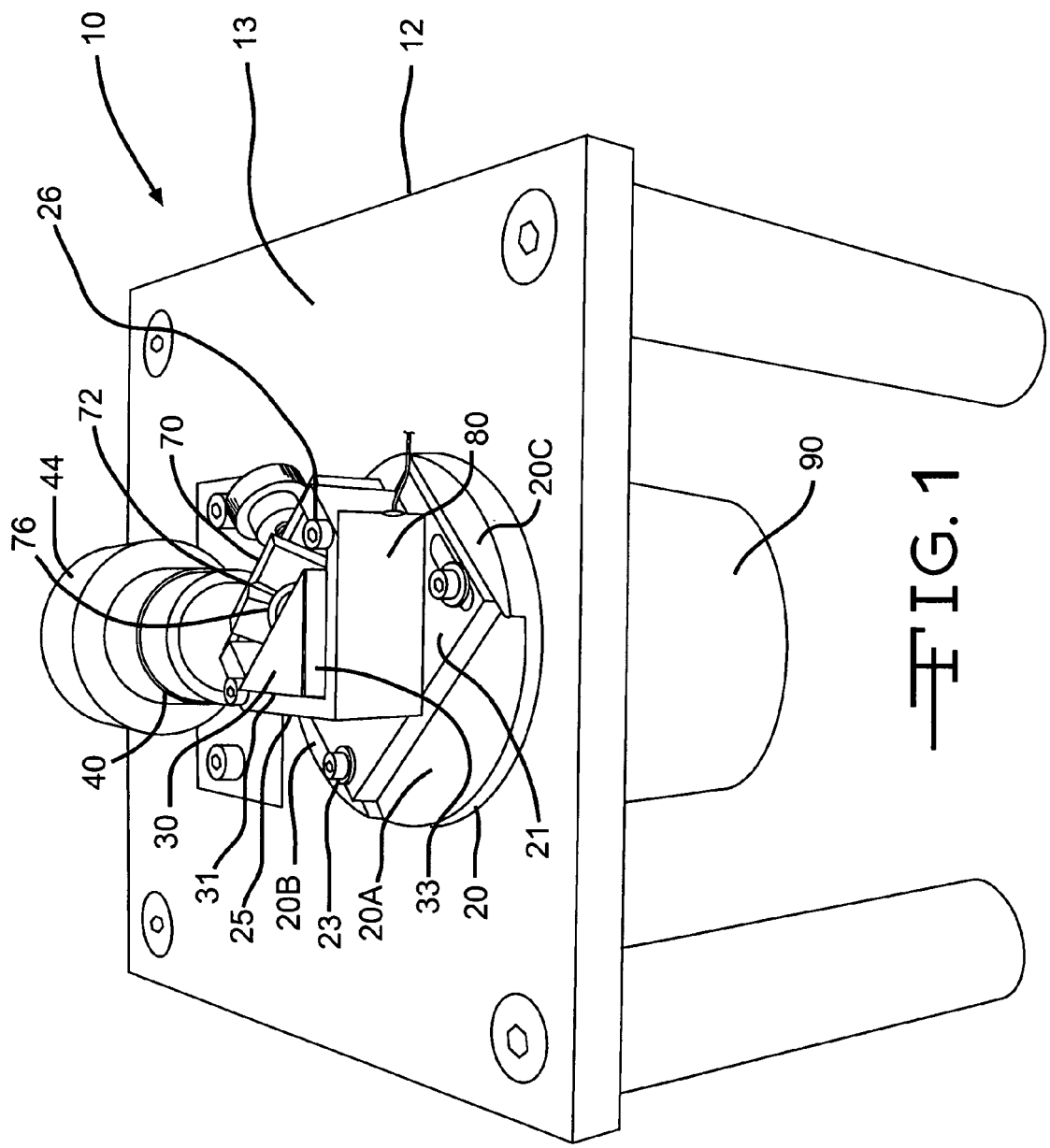
FIG. 1 is a perspective view of one embodiment of a preferred portable surface plasmon resonance biosensor device 10 of the present invention.
Figure 2:
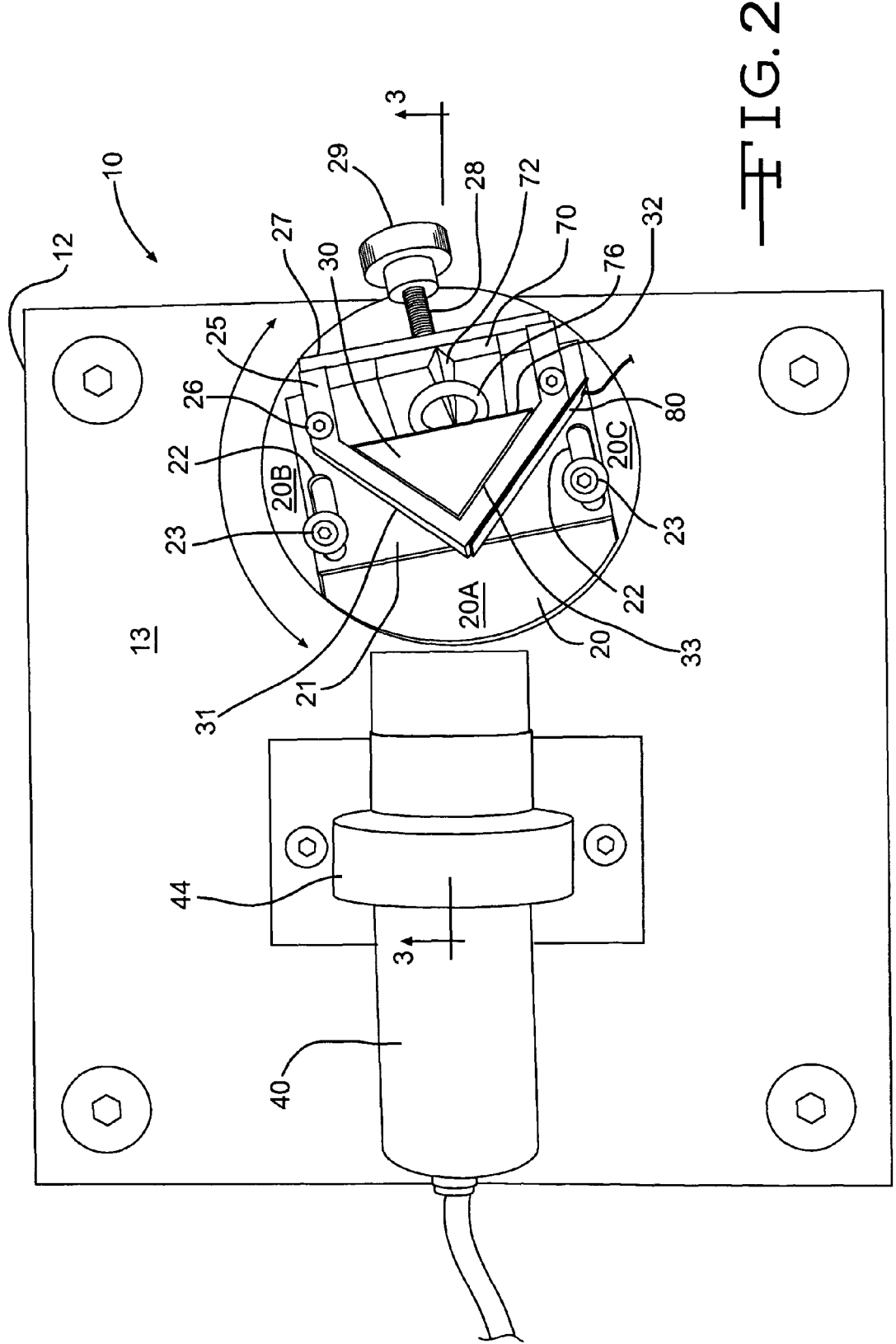
FIG. 2 is a top view of the surface plasmon resonance biosensor device 10 of FIG. 1.
Figure 3:
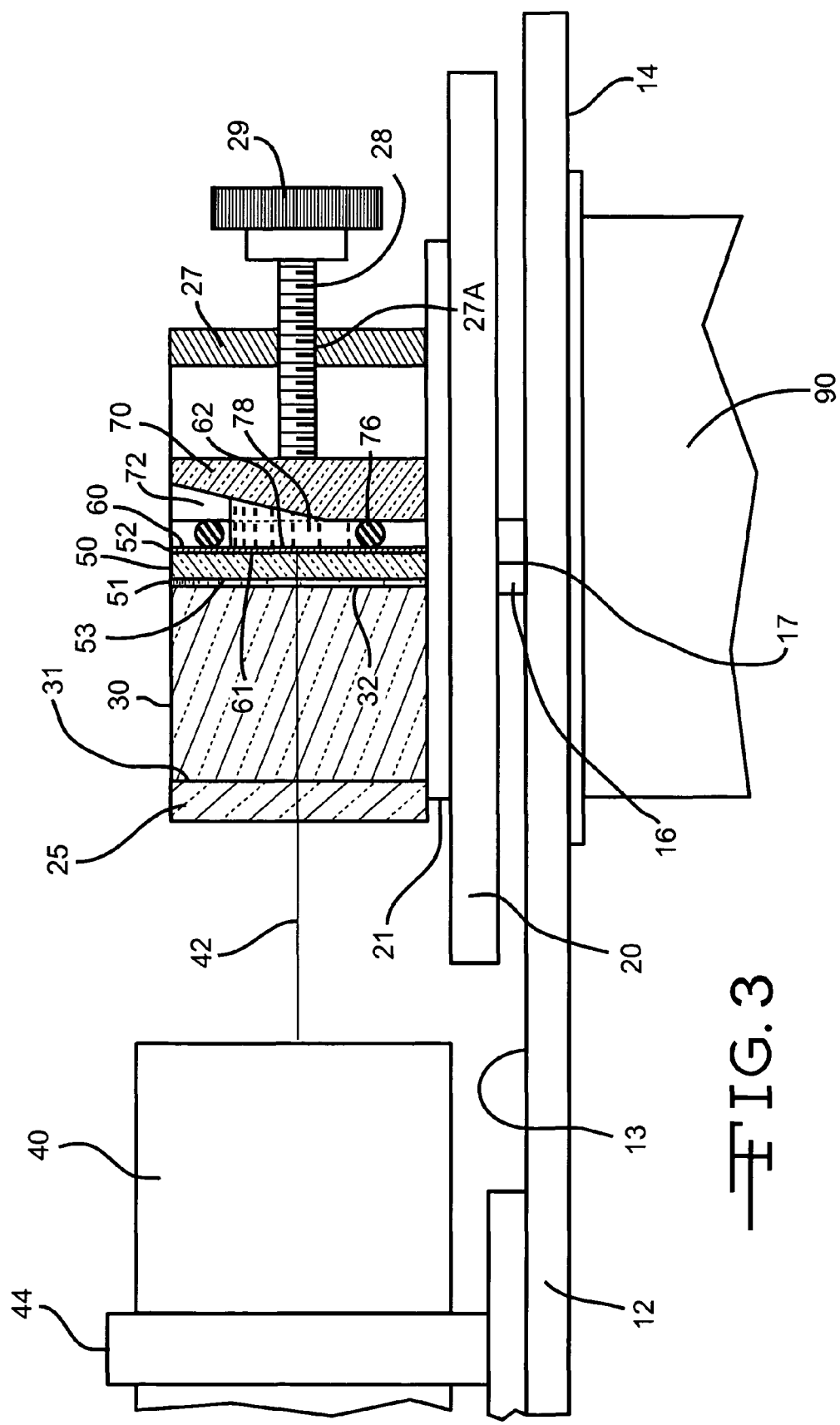
FIG. 3 is a cross-sectional view of the surface plasmon resonance biosensor device 10 of FIG. 2 taken along line 3-3.

One embodiment of the surface plasmon resonance biosensor device 10 of the present invention is illustrated in FIGS. 1-3. In this embodiment of the device 10, a mounting table 12 with a top surface 13 and a bottom surface 14 (FIG. 3) is used to support the components. A shaft 16, as seen in FIG. 3, of a capacitive angle sensor 90 is mounted through a hole (not shown) in the mounting table 12. One commercially available capacitive angle sensor that can be used is the Series 600 Angular Displacement Transducer (ADT) Model No. 0601-0000 (Transtek Inc., Ellington, Conn.). The capacitive angle sensor 90 is capable of measuring the rotation of the shaft 16 relative to the mounting table 12 to provide a first signal output. A rotatable plate 20 is mounted over the table 12 affixed on the top end 17 of the shaft 16. The bottom end (not shown) of the shaft 16 extends down into the body of the capacitive angle sensor 90 mounted on the bottom surface 14 of the mounting table 12. The rotatable plate 20 is free to turn with respect to the mounting table 12 as illustrated by the arrow in FIG. 2. On the top of the rotatable plate 20 is a depressed portion 20A disposed between two projecting ridges 20B, 20C at opposed ends of the rotatable plate 20. An adjustable base 21 having two slots 22 at opposed ends of the rectangular shaped adjustable base 21 is adjustably attached by a first set of Allen screws 23 in the depressed portion 20A of the rotatable plate 20 between the two projecting portions 20B, 20C. A V-shaped transparent holder 25 is mounted on the adjustable base 21 by means of a second set of Allen screws 26. A prism 30, for example a ZF7 glass uncoated right-angle prism (Red Optronics, Mountain View, Calif.), is placed within the V-shaped transparent holder 25 on the rotatable plate 20. A laser apparatus 40, for example a Melles Griot (Carlsbad, Calif.) 06 DAL 103 laser, is affixed to the top surface 13 of the table 12, positioned to project a beam of laser light 42 (FIG. 3) through a first side 31 of the prism 30 to a second side 32 as the base of the prism 30. The adjustable base 21 can be moved in a direction along the rotatable plate 20 to move the second side 32 of the prism 30 forwards or backwards so as to center it on the rotatable plate 20. Once the prism 30 is at the desired location, the first set of Allen screws 23 can then be tightened to secure the adjustable base 21 to the rotatable plate 20.

FIG. 3 illustrates the device set up to receive a fluid sample. A transparent cover 50 (illustrated in FIG. 3) is removably mounted to the prism 30 with a first side 51 of the transparent cover 50 mounted against the second side 32 of the prism 30. A thin coating of immersion oil 53 (illustrated with exaggerated thickness in FIG. 3) can be used to make a close seal between the prism 30 and the transparent cover 50. The transparent cover 50 has a thin metallic film 60 having an inner surface 61 affixed to a second side 52 of the transparent cover 50. The transparent cover 50 with the affixed thin metallic film 60 can be disposable. Thus, the surface plasmon resonance biosensor device 10 can be reused with a new and clean thin metallic film 60 after each use. An SPR sample holder 70 having an o-ring 76 is removably sealed against an exposed surface 62 of the thin metallic film 60. The SPR sample holder 70 holds the o-ring 76 firmly against the thin metallic film 60 by a screw 28 threaded through a hole 27A in a back plate 27. A user can thereby add pressure to secure the sample holder 70 by gripping the knob 29 and twisting the screw 28. When the screw 28 is tightened, the SPR sample holder 70, o-ring 76 and thin metallic film 60 form a sample chamber 78. A fluid sample can be placed into the sample chamber 78 through an opening created by a wedge-shaped cut 72 in the SPR sample holder 70. A solar cell 80, such as a Radio Shack® (Fort Worth, Tex.) silicon solar cell model 276-124, is mounted on the V-shaped transparent holder 25. The solar cell 80 is mounted adjacent to a third side of the prism 30 for measuring the laser light 42 intensity reflected from the inner surface 61 of the thin metallic film 60 and through the third side 33 of the prism 30.

Figure 4:
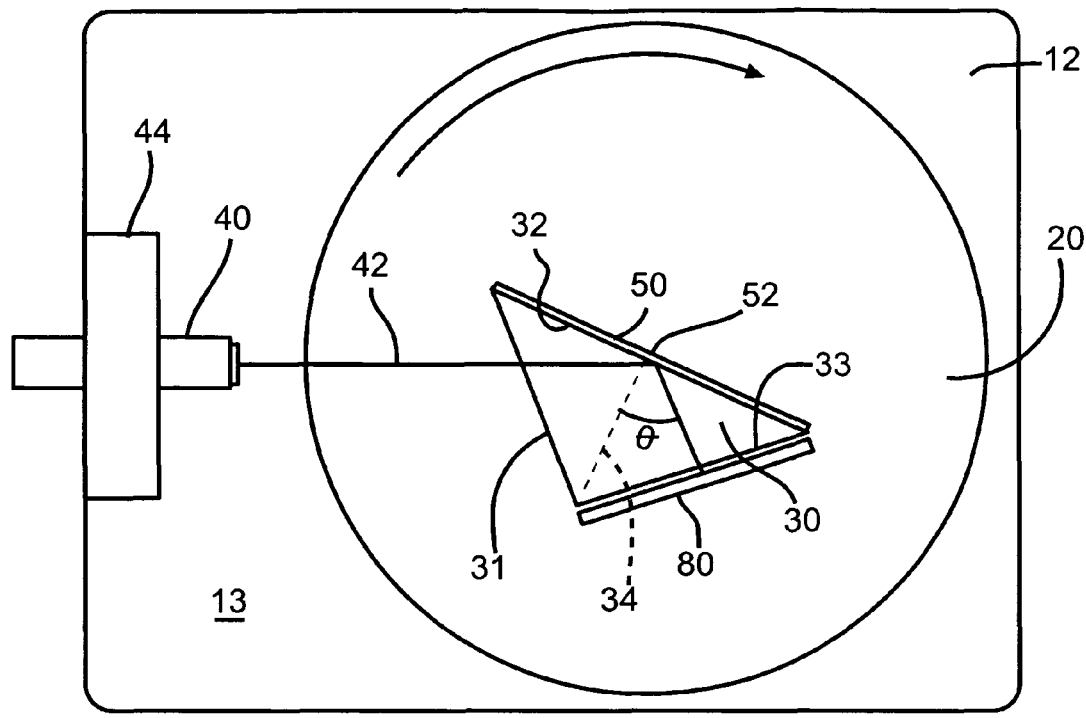
FIG. 4 is a schematic representation of a top view the surface plasmon resonance biosensor device 10 of FIG. 1 illustrating the incident angle θ of the laser beam 42 passing through the first side 31 to the second side 32 of the prism 30 and reflecting through the third side 33 onto the solar cell 80.

FIG. 4 is a schematic representation of a top view the surface plasmon resonance biosensor device 10 of FIGS. 1-3. The laser apparatus 40 is secured to the top surface 13 of the mounting table 12. When the laser apparatus 40 is activated, a beam of laser light 42 is emitted by the laser apparatus 40 which penetrates into the first side 31 of the prism 30. The beam of laser light 42 is then reflected back from the multiple layers shown in FIG. 9, penetrates the third side 33 of the prism and reaches the solar cell 80. The solar cell 80 transduces the reflected laser light 42 intensity into an electrical signal to provide an intensity output. FIG. 4 illustrates the incident angle θ, relative to a line 34 normal to the second side 32 of the prism, made by the laser beam 42 as it passes through the first side 31 to the second side 32 of the prism and reflects back through the third side 33 onto the solar cell 80. The capacitive angle sensor 90 (see FIGS. 1 and 3) mounted on the second end of the shaft 16 measures the incident angle θ (FIG. 4) of the laser light 42 with the thin metallic film 60 to provide an incident angle output.

To measure SPR spectra in a SPR biosensor device 10 with a monochromatic light source, a user must change the incident angle θ of the beam of laser light 42 in FIGS. 1-3. In the Biacore® system, a focused light beam is used, so that the incident light with different incident angle can be detected by a one dimensional light sensitive diode array. This optical system is expensive. In the SPR biosensor Dr. Xiao made in Tsinghua University (China), a θ~2θ goniometer from an x-ray diffraction machine was used to trace the reflected light spot, because the angle between the incident light and the reflected light changes 2dθ if the incident angle changes dθ. Goniometers used with x-ray diffraction machines are instruments used for precise measurement of angles of crystals. However, these goniometers have the drawbacks of being very expensive, heavy (>100 kg) and they give no electric signal that provides angle shift information.

Figure 5:
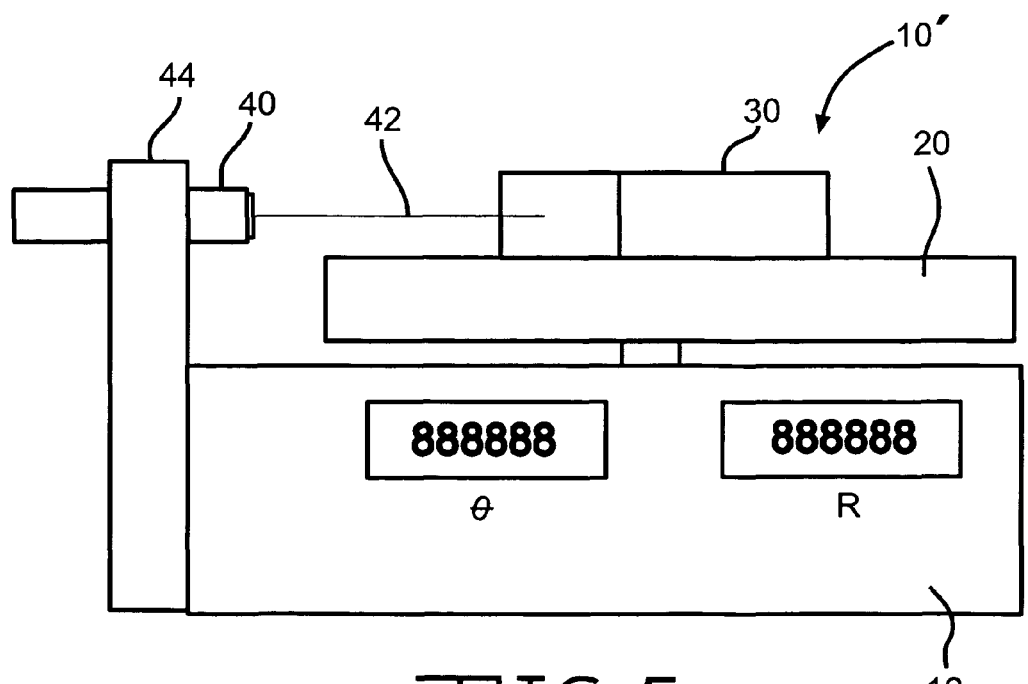
FIG. 5 is a schematic representation of a second embodiment of a surface plasmon resonance biosensor device 10' that electronically displays incident angle θ and R. A single chip computer is included inside the embodiment, so it can work without a personal computer.

In the portable SPR biosensor device 10 of the present invention, a commercial capacitance angle sensor 90 is used to measure the incident angle θ. With a fifteen volt direct current (15V DC) input, the capacitance angle sensor 90 can give an angle signal output of one hundred millivolts per degree (100 mV/Degree). The capacitance angle sensor 90 and a semiconductor laser 40 were both affixed to the body of an aluminum mounting table 12 as illustrated in FIGS. 1-3. The prism 30, made of N—SF6 (ZF7) glass, was fixed on the horizontal disk-shaped rotatable plate 20 coupled to the shaft 16 of the capacitance angle sensor 90. The rotation of the shaft 16 of the capacitance angle sensor 90 changes the incident angle θ of the beam of laser light 42 reflected inside of the prism 30. The reflected laser light 42 illuminates a spot on the solar cell 80 that will also move a distance of r×Δθ, where r is the distance between the solar cell 80 and the reflective laser light 42 spot in the prism 30, and Δθ is the angle shift for an SPR spectrum. Usually Δθ is less than 18°, r less than 30 mm, and the distance of the light spot on the moving solar cell 80 will be less than 10 mm. The reflected laser light 42 spot will not move off of the solar cell 80 that is turning with the prism 30. Tracing the reflected light spot in SPR biosensors is a novel part of the design. No expensive optical or mechanical devices are needed in the SPR biosensor device 10. FIG. 5 is a schematic representation of a second embodiment of a surface plasmon resonance biosensor device 10', otherwise identical to the surface plasmon resonance biosensor device 10 illustrated in FIGS. 1-3, additionally having displays for incident angle θ and R.

Figure 8:
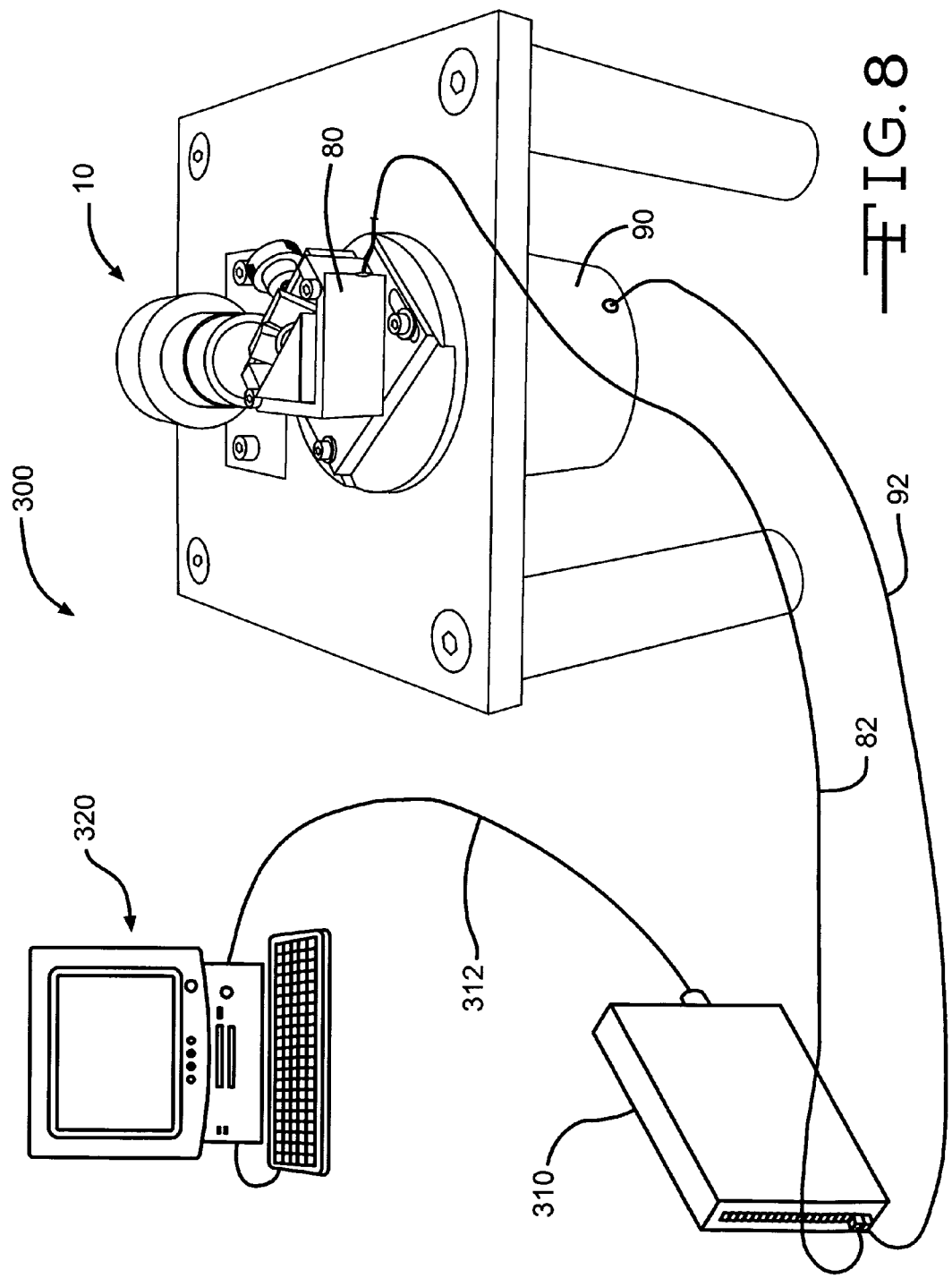
FIG. 8 is another embodiment of a surface plasmon resonance biosensor system 300 having the surface plasmon resonance biosensor device 10 of FIG. 1 electrically connected to a personal computer 320 to receive and process data from a data acquisition device 310.

FIG. 8 is one embodiment of a surface plasmon resonance biosensor system 300 having the surface plasmon resonance biosensor device 10 of FIG. 1 electrically connected to a personal computer 320 to receive and process data from a data acquisition device 310. There are two analog DC signal outputs from the SPR biosensor device 10. The first signal output is from the capacitance angle sensor 90, and the second signal output is from the solar cell 80. It is easy to use any commercially available USB data acquisition device 310, such as a Personal Measurement Device™ brand USB-based analog and digital I/O module PMD-1608FS (Measurement Computing Corporation, Norton, Mass.) to record the two analog signals for collecting an SPR spectrum. LabVIEW® development software (National Instruments, Austin, Tex.) can be used to write software to control the SPR biosensor device 10, however other software can be used. The optical layout of the SPR biosensor device is illustrated in the magnified view of FIG. 9. A transparent cover 50 of glass, gold (Au) as the thin metallic film 60, and a bound sample layer 66 constituted a sensitive chip. The chip was stuck to the base, that is the second side 32, of the prism 30 by immersion oil 53 (see FIG. 3). A rubber o-ring 76 and Teflon® polytetrafluoroethylene (PTFE) chuck as the sample holder 70 were pressed to the sensitive chip, thereby forming a two hundred microliter (200 μl) volume sample chamber 78 (see FIG. 3). In some embodiments, there can be two channels in the sample holder 70 for pumping a fluid sample (ie. liquid or gas) into the sample chamber 78. In the SPR system shown in FIG. 9 there are five optical medium: the prism 30, the transparent cover 50, the gold as the thin metallic film 60, the bound sample layer 66 and the liquid buffer 68. The prism 30 was made from a piece of ZF7 glass. Its refractive index value at 650 nm was 1.798. The refractive index of microscope glass as the transparent cover 50 was 1.56. The refractive index of the gold as the metallic film 60 at 650 nm was 0.204+i3.484. The buffer refractive index was chosen as 1.331 for water at room temperature.

Figure 12A:
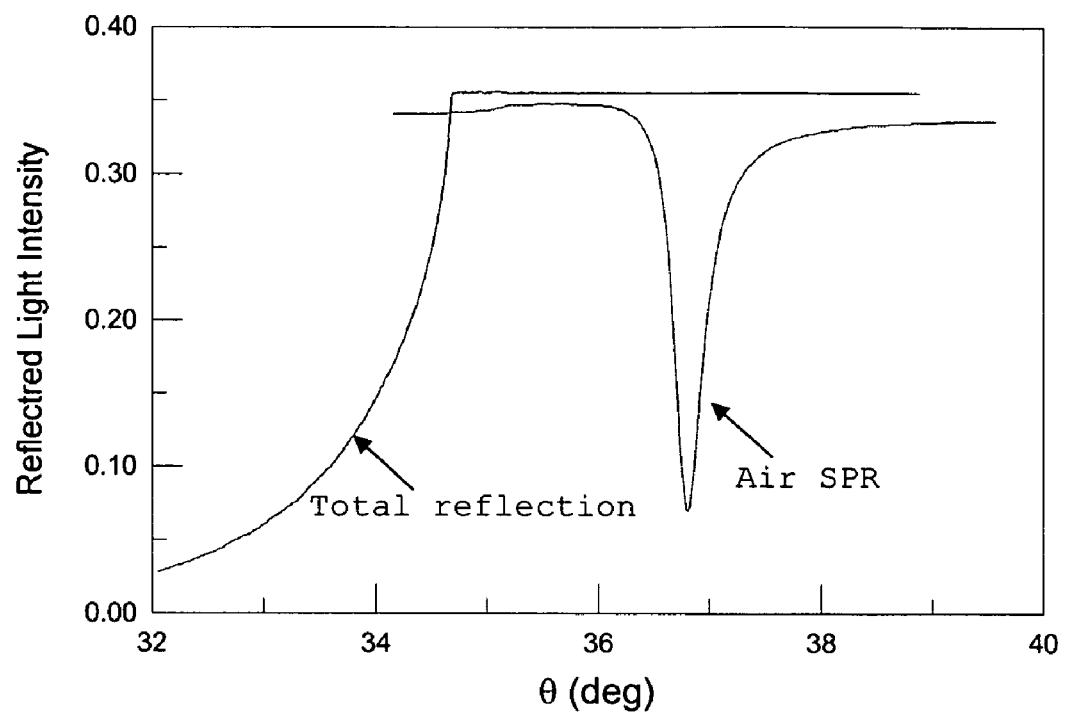
FIG. 12A is a graph illustrating a total reflection curve and a SPR spectrum in air.
Figure 12B:
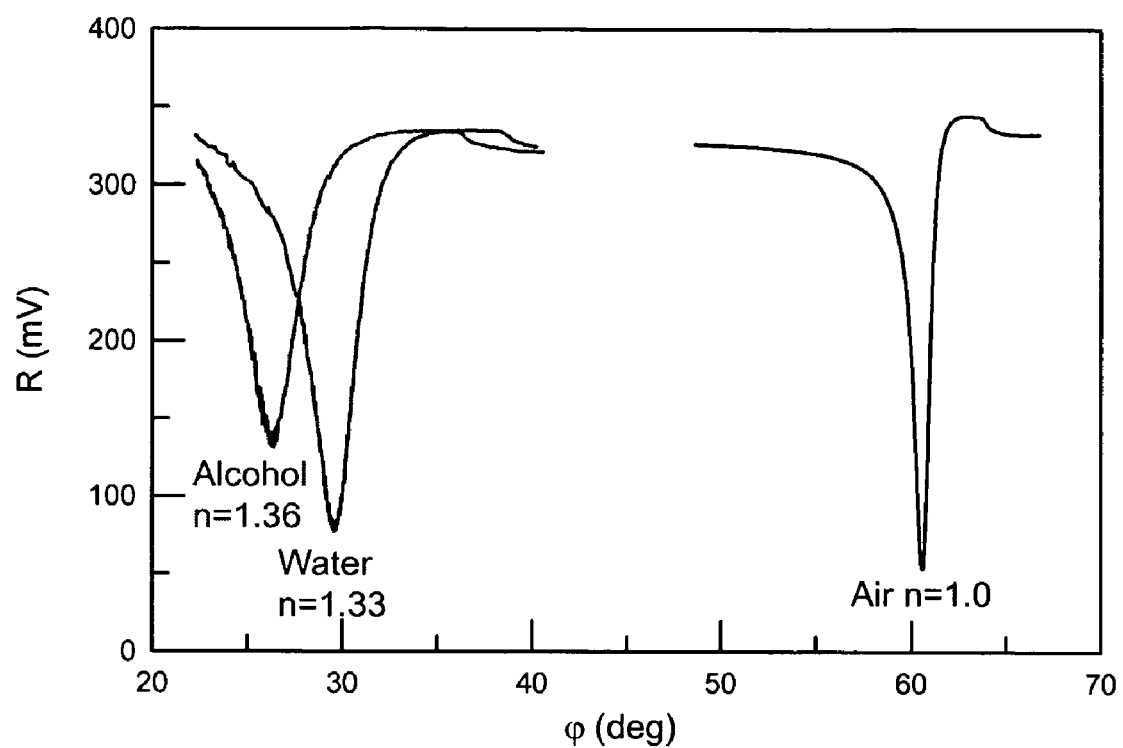
FIG. 12B is a graph of three SPR spectra (reflected light intensity versus the outside incident angle φ) directly measured by the surface plasmon resonance biosensor 10 of FIG. 1.
Figure 12C:
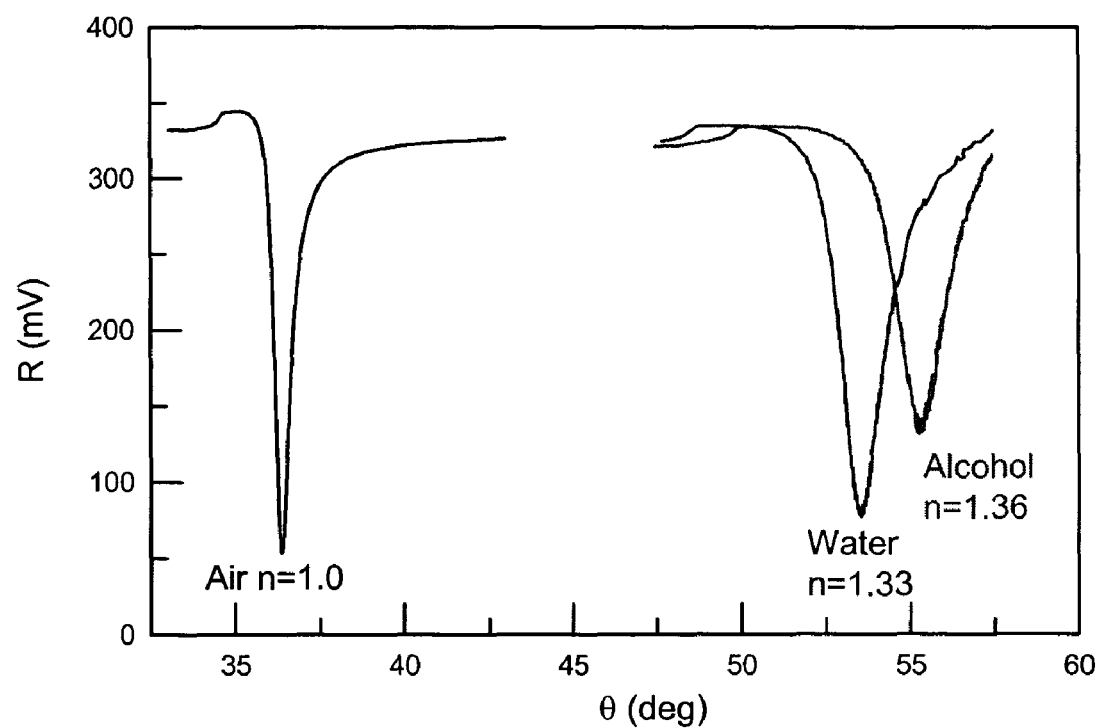
FIG. 12C is a graph of three surface plasmon resonance spectra (reflected light intensity versus the inside incident angle θ) that is derived from FIG. 12B.
Figure 14:
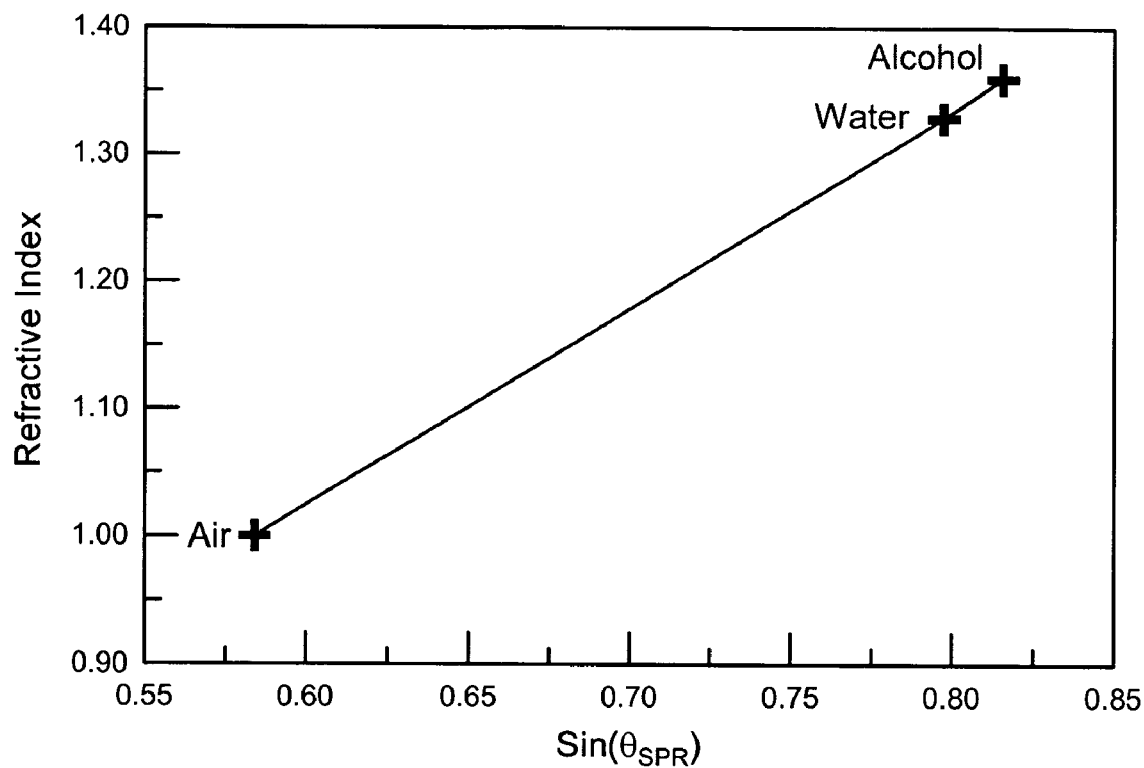
FIG. 14 is a standard plot using experiment data from the surface plasmon resonance biosensor 10 of FIG. 1. This linear relationship shown in the graph can be used to measure refractive index of samples

While measuring the spectra shown in FIG. 12C, there was no sample layer 66 film on the gold metallic film 60 surface of the sensing chip. Air, water or alcohol as the media was in direct contacted with the chip. By manually turning the rotatable plate 20 illustrated in FIG. 1-FIG. 3, the SPR spectra was obtained. The resonance angle ($\theta_{SPR}$) increases from 36.34°, 53.49° to 55.26° in response to the refractive index change of the media contacting the gold metallic film 60 surface from 1.000, 1.331 to 1.360. From our calculations, the SPR biosensor device 10 can be used to measure refractive index (n, 1.0 to 1.4) of both gases and liquids as the fluid sample using the standard plot of FIG. 14. The relationship between $\theta_{SPR}$ and n is shown in Equation 1.

$$n = 1.549 \sin(\theta_{SRP}) + 0.095 \qquad \text{Equation 1}$$

Figure 13:
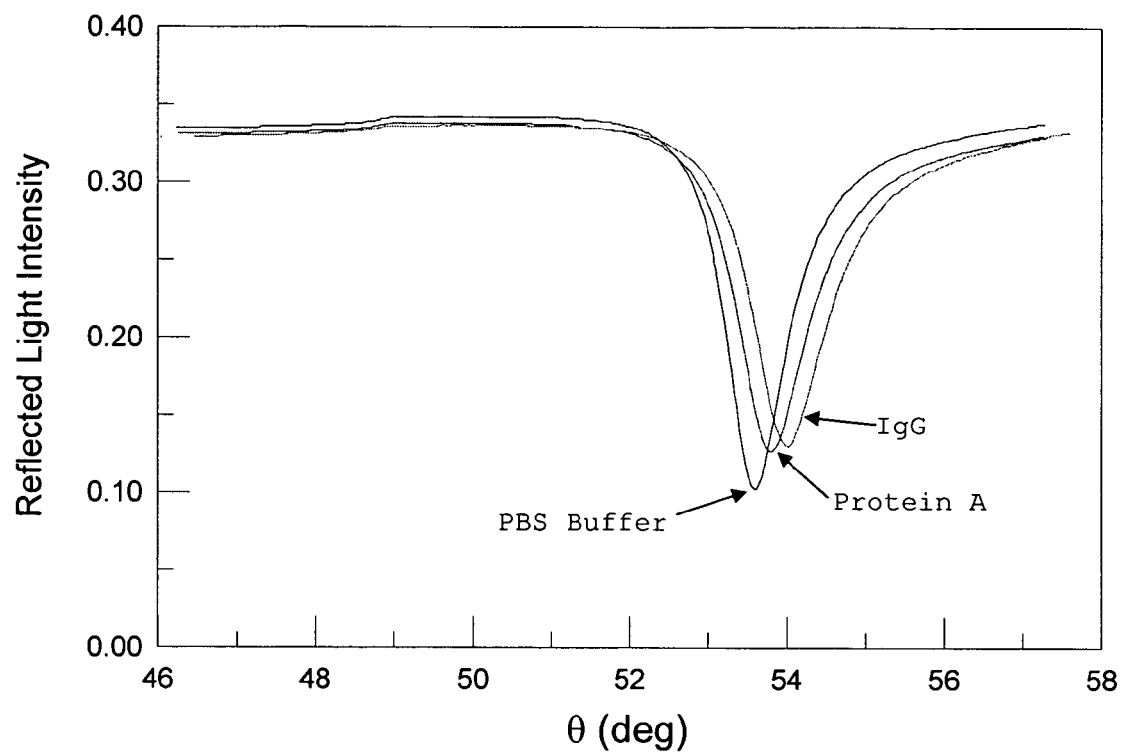
FIG. 13 is a graph of three surface plasmon resonance spectra measured by the SPR biosensor device 10 of biological samples. IgG antibody specifically binds to Protein A immobilized on the gold surface of the metallic film immersed in Phosphate Buffered Saline (PBS) buffer in the sample chamber 78. "PBS Buffer": PBS sample buffer alone. "Protein A": Protein A immobilized on the gold surface in a PBS sample buffer. "IgG": IgG antibody binding to Protein An immobilized on the gold surface in a PBS sample buffer.

FIG. 12A is a graph of a total reflection curve and a SPR spectrum in air measured by the SPR biosensor device 10 of the present invention illustrated in FIG. 1-FIG. 3. FIG. 12B is a directly measured graph of reflected light intensity versus the outside incident angle φ, while FIG. 12C is a graph of the surface plasmon resonance spectra. FIG. 12C shows three SPR spectra measured by the SPR biosensor device 10 of the present invention for air, water and alcohol. FIG. 13 shows SPR spectra of biological molecular interactions on a gold metallic film 60 surface immersed in phosphate buffered saline (PBS) buffer. After the SPR spectrum of the gold metallic film 60 in the PBS buffer was obtained (labelled "PBS Buffer"), Protein A solution (10 μL×2 mg/mL) was injected into the sample chamber 78 with 150 μL of PBS buffer. Ten minutes later, the sample chamber 78 was washed and refilled with PBS buffer, and the SPR spectrum labelled "Protein A" was measured. At last 10 μl, goat serum with antibody was injected into the sample chamber 78. After washing and refilling the sample chamber 78 with PBS buffer, the SPR spectrum labelled "IgG" was obtained. We can see that protein molecules adsorbed on the gold surface shifted the SPR spectra from left to right. From numerical simulations it was found that there was a linear relationship between protein surface concentration Γ (ng/mm²) and SPR resonance angle shift $\theta_{SPR}$ (degree).

$$\Gamma = 8.55\Delta\theta_{SPR} \text{ or } \Gamma = -4.70\Delta\phi_{SPR}$$

Figure 6:
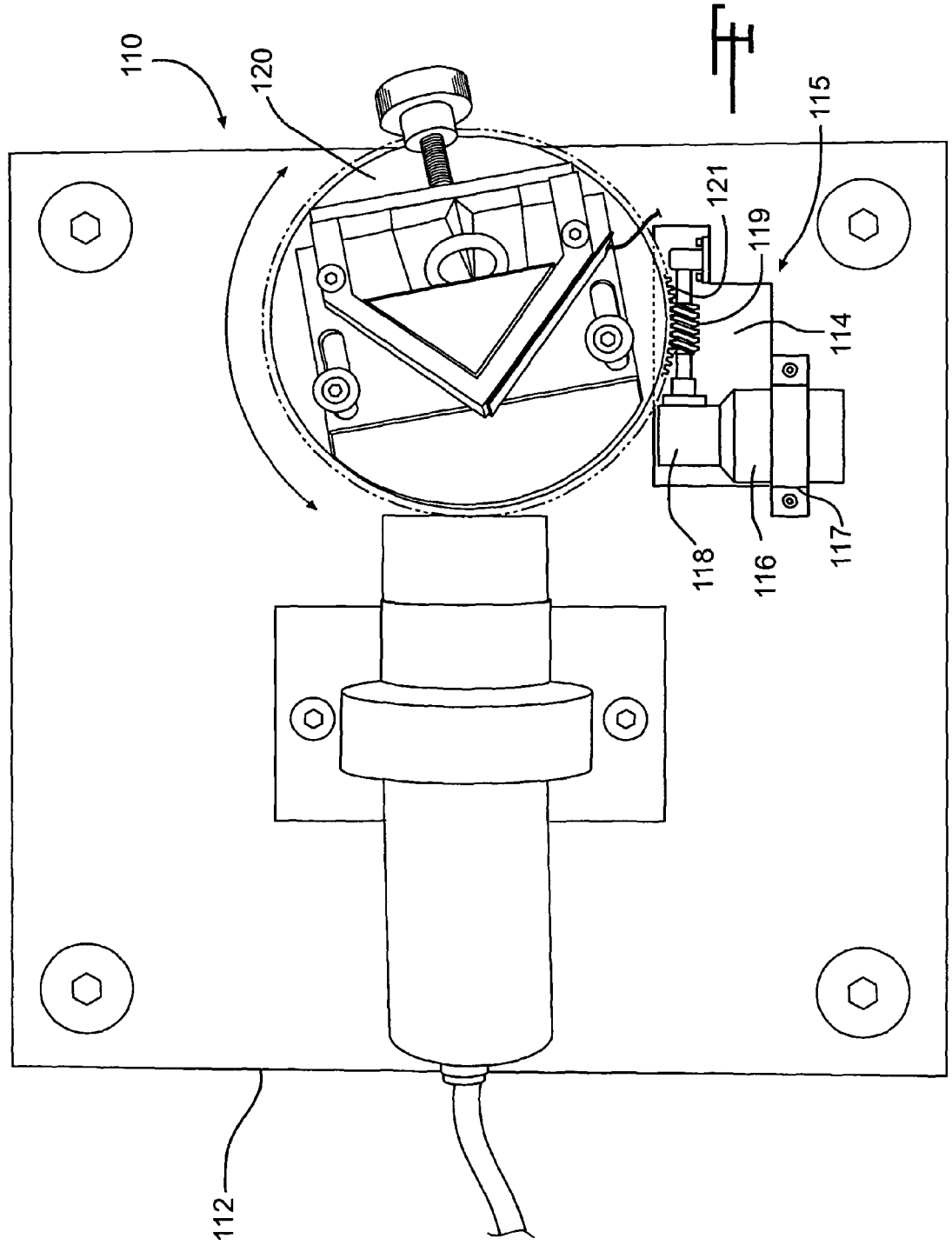
FIG. 6 is a top view of a third embodiment of a surface plasmon resonance biosensor device 110 of the present invention having a low-speed motor to turn the rotatable plate 120 in small increments.

With these formula, the portable SPR biosensor can measure affinity constants about ligand-receptor interactions. In one embodiment, the incident angle θ is changed manually. The SPR biosensor device 10 in this embodiment can be used to use as a teaching instrument to teach students about SPR and how to measure liquid refractive index and antigen-antibody interactions. Optionally, in a second embodiment as illustrated in FIG. 6, a low speed motor 116 can be installed as a drive system 115 on the aluminum table 12 shown in FIG. 1-FIG. 3, so the scan angle can be automatically processed.

The low speed motor 116 is mounted in a depression 114 in the table 12 by means of a mount 117. A gear box 118 transmits power to a screw gear 119 that meshes with teeth 121 on the outer perimeter of the rotatable plate 120. Otherwise the biosensor device 110 is identical to the biosensor device 10 of FIG. 1-FIG. 3. With automatic angle scanning and any commercially available liquid injection system (not shown), the homemade SPR biosensor device 110 can be used as a professional research instrument in universities and hospitals. For example, the SPR biosensor device 10 can be used to detect tumor marker proteins or AIDS virus proteins in a patient's blood serum within one minute without the necessity of labeling or treating the sample. Only ten microliters (10 μL) of serum is enough to use in measurements for clinical diagnosis.

Figure 9:
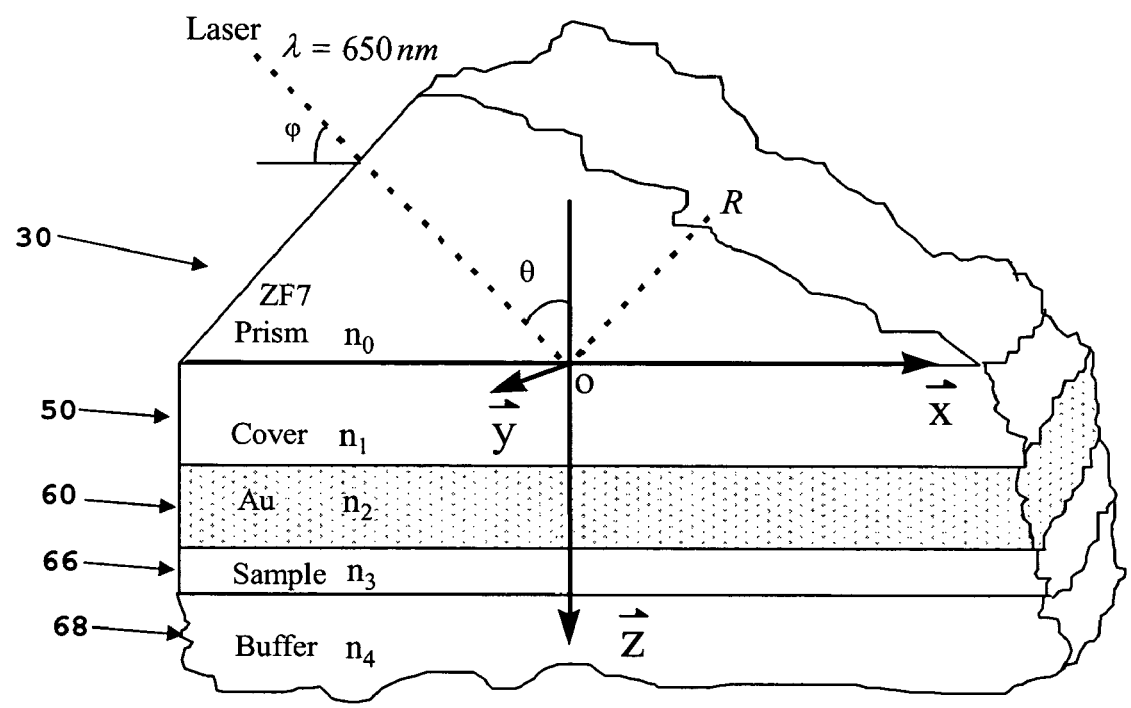
FIG. 9 illustrates a magnified view of the optical media and optical path of the plasmon resonance biosensor device 10 of FIG. 1.
Figure 11:
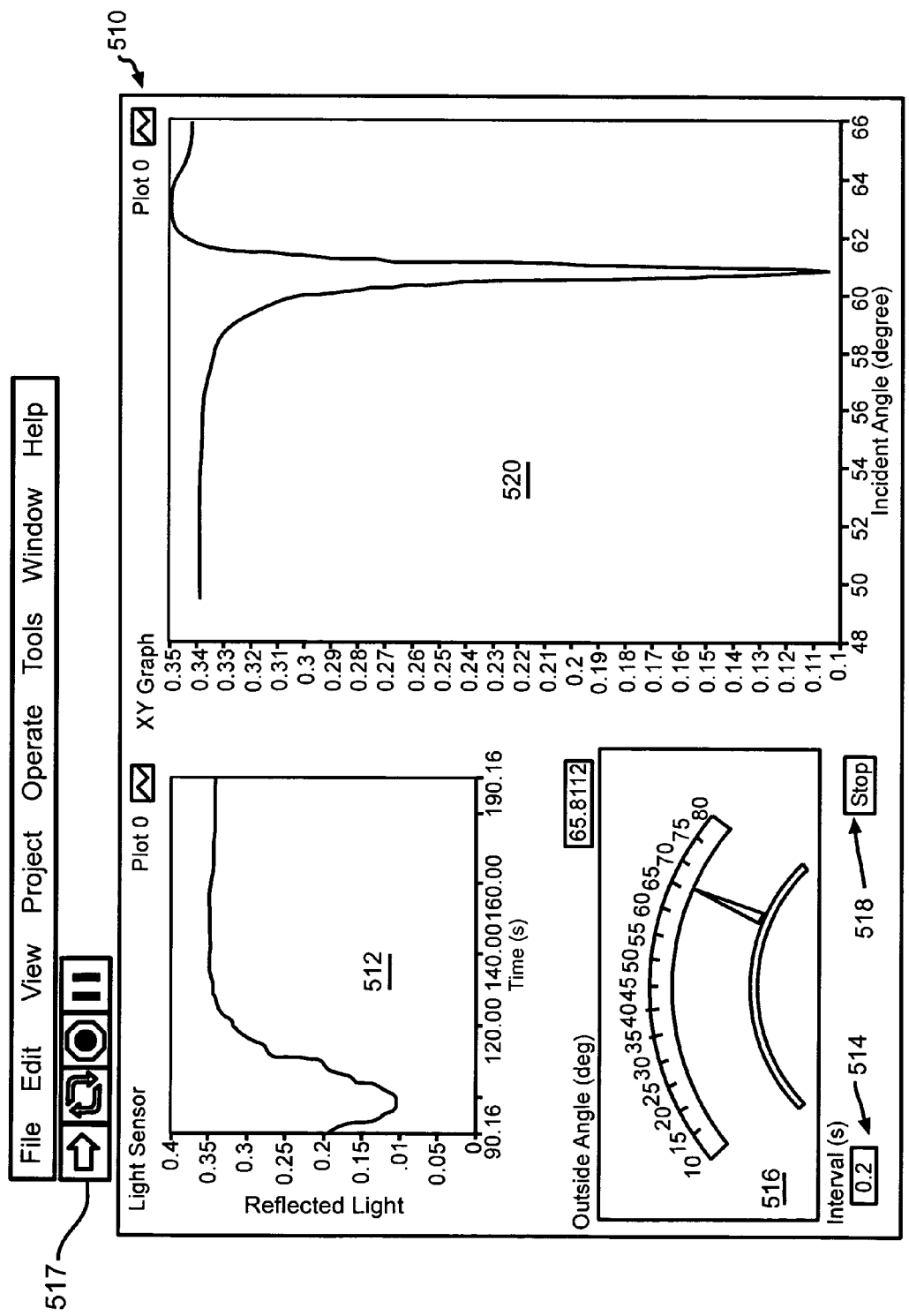
FIG. 11 is a display screen of the interface 510 generated by the software illustrated schematically in FIG. 10.

Software for analysis of output signals was written with Labview® for PC. The interface 510 shown in FIG. 11 was obtained by pressing the "Print Scrn" key on the PC computer 320 keyboard after measurement with gold as the metallic film 60 with air in the sample chamber 78. On the upper-left corner of the interface 510 there is a light sensor graph 512 which records the relationship between the solar cell voltage and time. The time interval 514 of each point on the light sensor graph 512 is 0.2 seconds as shown on the lower-left corner of the interface. However, the interval can be changed by the user. Below the light sensor graph 512 there is a virtual meter called the outside angle meter 516. The outside angle is the angle φ between the laser and the base of the prism 30 as illustrated in FIG. 9. The outside angle φ is the angle directly measured by the angle sensor 90 shown in FIG. 1. The relationship between φ and the inside angle θ is:

$$\theta = 45° + \arcsin\left[\frac{1}{n_0}\sin(45° - \varphi)\right] \qquad \text{Equation 3}$$

where the parameter $n_o$ is the refractive index of the prism. At λ=650 nm, the refractive index of the prism is 1.798. The measurement is started by pressing the arrow tool button 517 on the second row of the software interface, as shown in FIG. 11. The angle φ was changed by the left hand of the user, and both the angle and the reflected light intensity is seen in real time. After the stop button 518 on the lower-middle of the interface is pressed, the measurement is stopped. The angle φ and light intensity parameters are combined to form the SPR spectrum shown in the XY graph 520 on the right of the screen. From optical theory the total reflection angle of the system should be $\theta_c = \arcsin(1/n_o) = 33.792°$. From FIG. 11, the outside total reflection angle $\phi_c = 64.000°$. According to Equation 3, the measured total reflection angle is $\theta_c = 33.012°$. The difference between the theory and measurement is 0.780°. The error might come from the angle sensor position for φ=0°, because it is difficult to exactly find 0° by eye.

Figure 10:
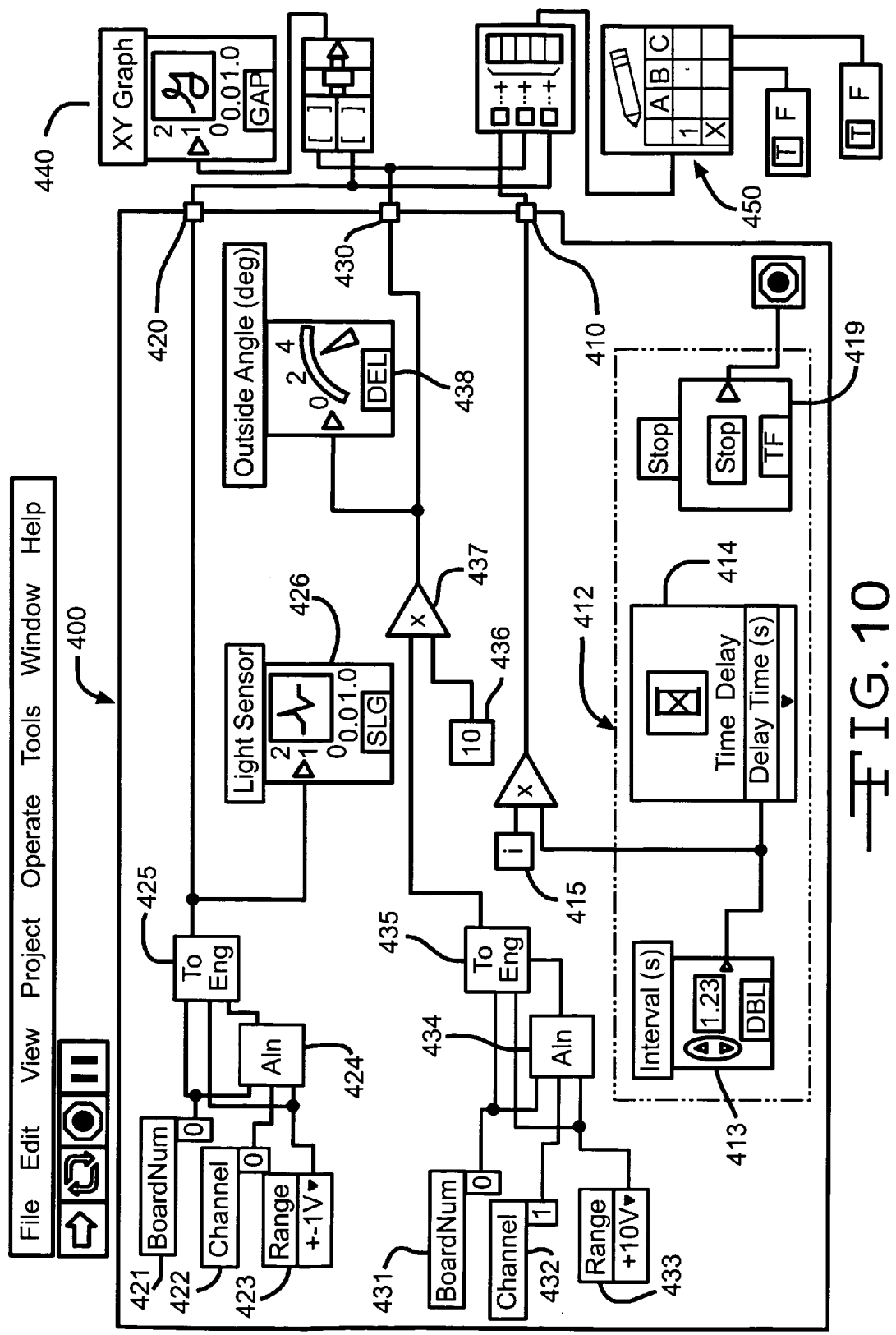
FIG. 10 is a schematic block diagram 400 of the software setup which provides the surface plasmon resonance spectra from the surface plasmon resonance biosensor device 10.

The SPR vi Block Diagram 400 is illustrated in FIG. 10. To provide a time output 410, a white-loop 412 is performed by setting an interval time 413 and a time delay 414 which will stop cycling when the stop button 411 on the front interface is pressed. A white-loop cycle sequence number (i) 415 is set. The output time (t) 410 is then computed by the formula: t=i×interval time. The interval of each cycle is 0.2 seconds by default, however users can change the interval. In each cycle, the program reads the reflected light intensity from the solar cell 80 and the prism 30 position from the capacitance angle sensor 90.

The light intensity output 420 is provided by setting the hardware number ("BoardNum") 421 from the USB-1608FS data acquisition device (DAQ), channel number ("Channel") 422, and analogous signal range (−1V to +1V) 423. Next, a sub-program 424 from the USB-1608FS data acquisition device which has eight channels (0, 1 . . . 7) for analog signal input. The sub-program 424 converts the analog voltage on channel 0 (the solar cell 80) to a 16-bit digital number. Then another sub-program 425 converts the 16-bit digital number to a scientific number for voltage. The next light sensor sub-program 426 displays an intensity versus time (R-t) graph on the front interface.

The angle output 430 is provided by setting the hardware number ("BoardNum") 431 from the USB-1608FS data acquisition device (DAQ), Channel Number ("Channel") 432 for the angle sensor, and analog signal range ("Range") 433 from −10V to +10V. A sub-program 434 from USB-1608FS data acquisition device converts the analog voltage on channel 1 (ie. the angle sensor 90) to a 16-bit digital number. Next, a sub-program 435 converts the 16-bit digital number to a scientific number in voltage. An amplification setting 436 of 10 to the sub-program 437 will result in the angle sensor 90 providing a one volt direct current (1.0V DC) signal if the angle of the shaft rotates ten (10) degrees. The sub-program 437 converts voltage to degrees. The outside angle sub-program 438 then displays angle versus time (angle-t) graph on the front interface. During an experiment, data provided at the light intensity output 420, the prism angle output 430, and the time data output 410 are each stored in a memory buffer. After the stop button 411 on the front interface is pressed, the light intensity data and prism angle data are combined to draw an SPR spectrum ("XY Graph") 440. The light intensity, prism angle and time data are combined to a data sheet 450 for file recording.

Figure 7:
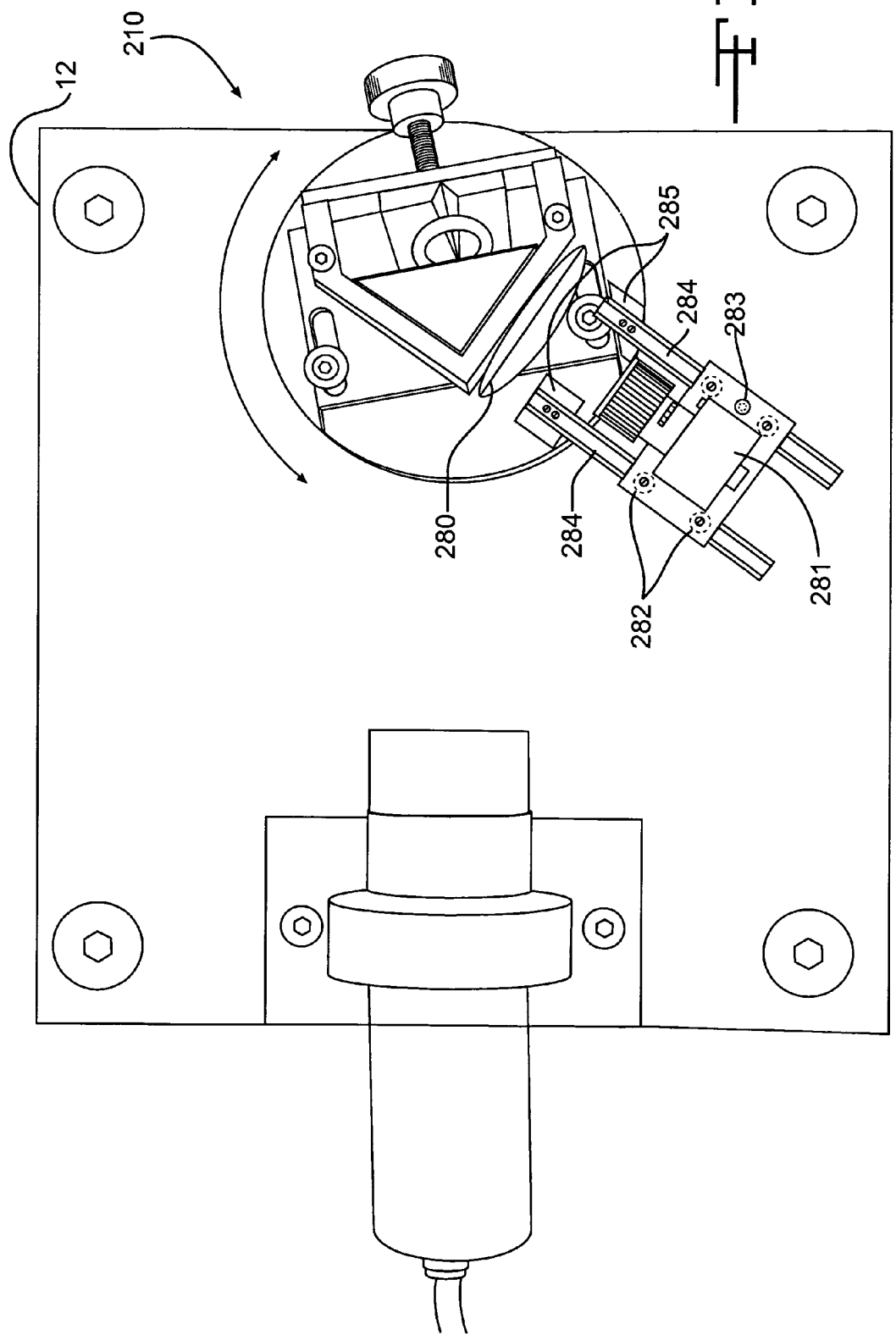
FIG. 7 is a top view of a fourth embodiment of a surface plasmon resonance biosensor device 210 of the present invention set up as an SPR microscope.

The portable SPR biosensor device (10, 110) with modifications, can also be used as a surface plasmon microscope (SPM) (Rothenhäusler, B. and W. Knoll, Surface plasmon microscopy. Nature, 1988. 332: p. 615-617). FIG. 7 is a top view of a fourth embodiment of a surface plasmon resonance biosensor device 210 of the present invention set up for use as an SPR microscope. By using a lens 280 (focus~20 mm) instead of the solar cell 80, and using a CCD camera 281 (2000 mm away), a ×100 microscope based on surface plasmon resonance is provided. (Zhou, Y., X. Caide, and S. F. Sui, Assembly of supported membranes studied by surface plasmon microscopy. Molecular Crystals And Liquid Crystals Science And Technology Section A Molecular Crystals And Liquid Crystals, 1999. 337: p. 61-64). The lens 280 projects laser light to the CCD camera 281 adjustably mounted on rollers 282 in rails 284, so that the CCD camera 281 can be moved nearer or farther from the lens 280. The rails 284 are mounted on elevator blocks 285 to the rotatable plate 20 described previously. When the CCD camera 281 is at the desired distance from the lens 280, it can be locked in place with a locking knob 283. This fourth embodiment of the SPM biosensor device 10 can be used to directly see a molecular monolayer in real time.

The portable SPR biosensor device 10, 110 of the present invention can be easily integrated with various electrochemical techniques, such as voltammetry. In this hyphenated technique, the SPR gold electrode can be also used as working electrode for an electrochemistry study. As a result, additional control and information can be applied and obtained from the gold SPR electrode. The combination of SPR with electrochemistry can provide correlations between electrochemically induced refractive index changes at electrode surfaces and the charge consumed in the process, for example electric deposit of conductive polymer, its stoichiometry, and the efficiency of the usage of charge in its deposition). It can also selective oxidize and reduce the analyte or ligand immobilized. Even though electrochemistry and SPR have been used together in the literature, the current SPR biosensor device has the additional advantage and convenience to be integrated comparing to the commercial instruments since in the portable SPR biosensor, all the components are easy to change and to access. Commercial instruments are often a black box and very hard to change anything.

Figure 20:
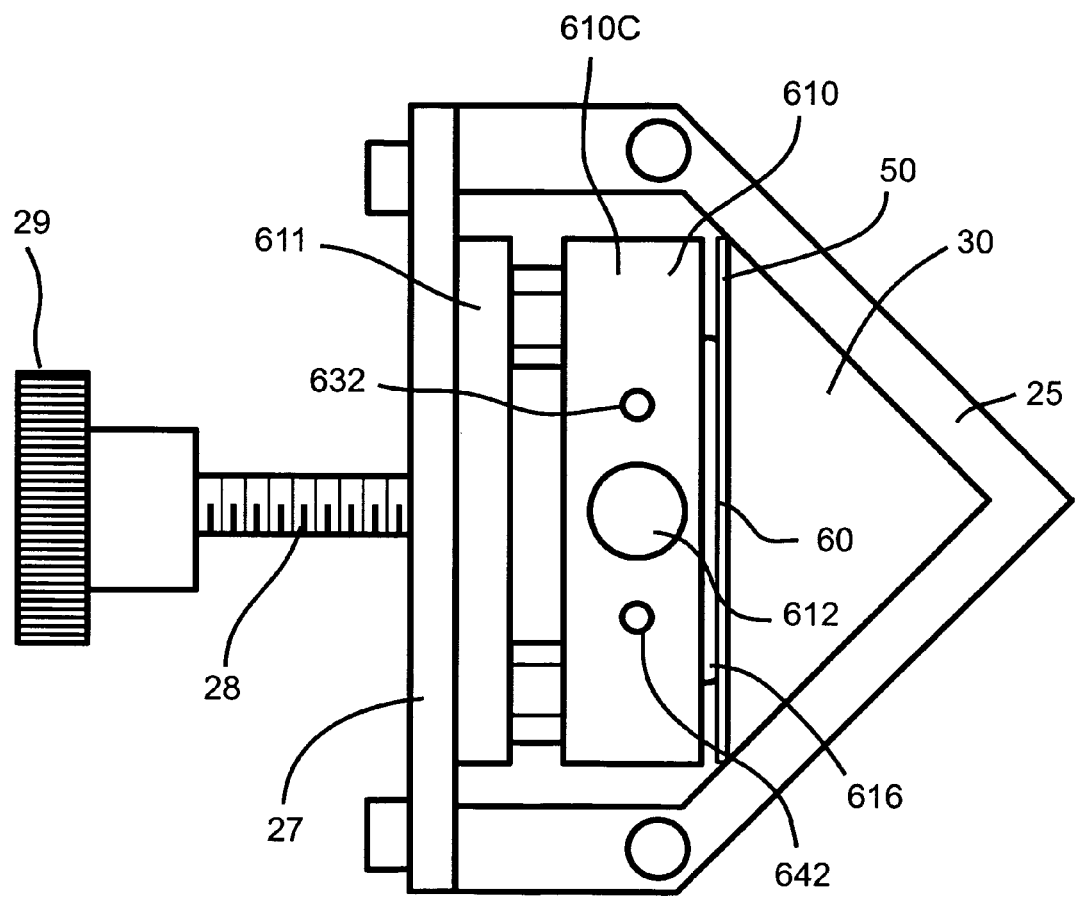
FIG. 20 is a top view of the V-shaped holder 25 of the surface plasmon resonance biosensor device 10 with a dual SPR/QCM sample holder 610 replacing sample holder 70.
Figure 21:
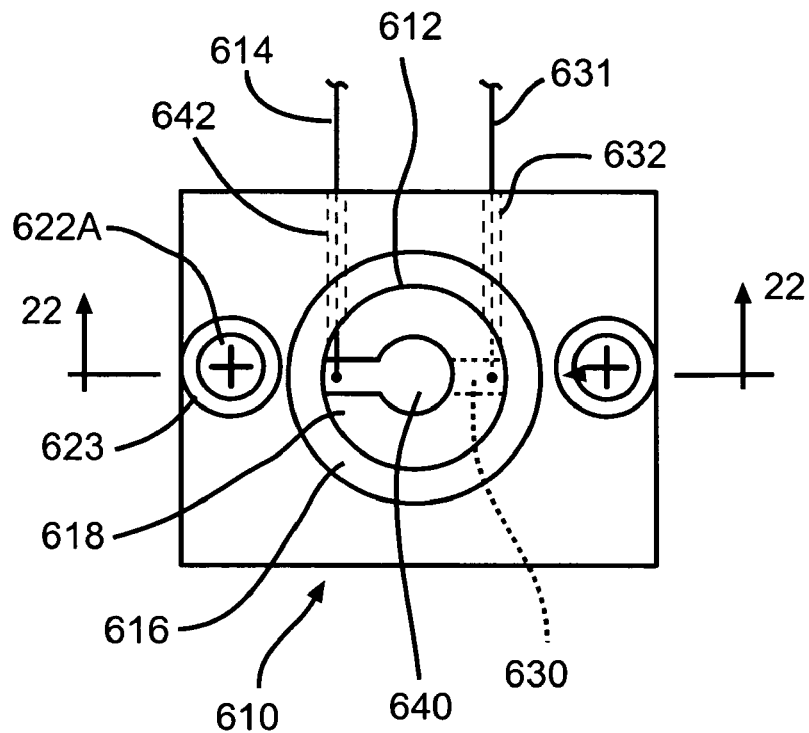
FIG. 21 is a front view of the dual SPR/QCM sample holder 610 of FIG. 20.
Figure 22:
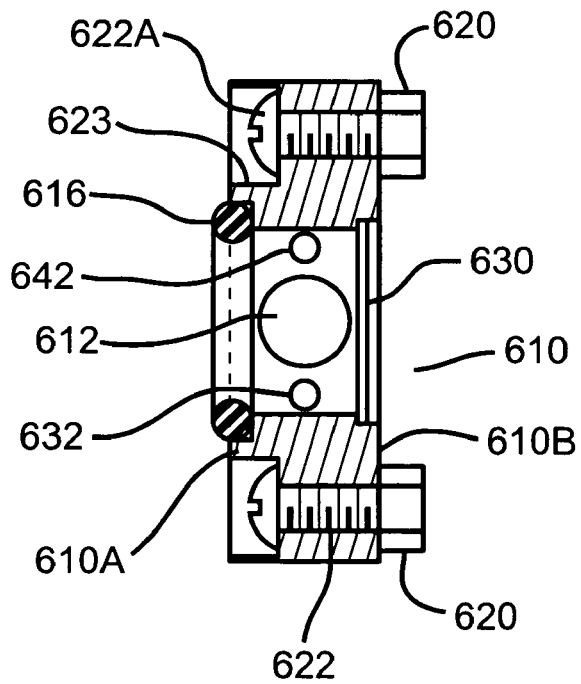
FIG. 22 is a cross-sectional view of the dual SPR/QCM sample holder 610 taken along line 22-22 of FIG. 21.

A further embodiment of the present invention is illustrated in FIG. 20, FIG. 21 and FIG. 22 that incorporates a quartz crystal microbalance (QCM) in a dual SPR/QCM sample holder 610. U.S. Patent Publication No. 2005/0003560 (application Ser. No. 10/861,617) to Zeng et al., which is hereby incorporated herein by reference in its entirety, is one example of a piezoimmunosensor as the QCM that can be incorporated into the dual SPR/QCM sample holder 610 of the present invention. In this embodiment, the SPR biosensor device 10, 110 is as described previously, except that the sample holder 70 is replaced with a dual SPR/QCM sample holder 610. The transparent cover 50 is removably mounted to the prism. The thin film of immersion oil (not shown) can be used for optical match between the prism 30 and the transparent cover 50. The thin metallic film 60 is affixed to the transparent cover 50. The dual SPR/QCM sample holder 610 has an o-ring 616 at a first side 610A of the dual SPR/QCM sample holder 610 that can be removably sealed against an exposed surface of the thin metallic film 60. The dual SPR/QCM sample holder 610 holds the o-ring 616 firmly against the thin metallic film 60 by the screw 28 threaded through the hole 27A (as shown in FIG. 3) in the back plate 27. When tightened, the screw 28 applies pressure to a spacer plate 611. A user can secure the dual SPR/QCM sample holder 610 by gripping the knob 29 and twisting the screw 28. When the screw 28 is tightened, the dual SPR/QCM sample holder 610, o-ring 616 and thin metallic film 60 form a sample chamber 618 (see FIG. 22). A fluid sample can be placed into the sample chamber 618 through an opening 612.

When the screw 28 is tightened against the spacer plate 611, the spacer plate 611 is held away from the dual SPR/QCM sample holder 610 by two nuts 620 protruding from a back side 610B of the dual SPR/QCM sample holder 610 that are threaded into two screws 622 passing through the dual SPR/QCM sample holder 610. The head 622A of each of the two screws 622 are countersunk in a cavity 623 in the front side 610A of the dual SPR/QCM sample holder 610, so that the head 622A of the two screws 622 do not interfere with the seal of the o-ring 616 against the thin metallic film 60. A quartz crystal 630 at the back side 610B of the dual SPR/QCM sample holder 610 provides a back wall of the sample chamber 618. The two nuts 620 keep the spacer plate 611 from contacting the quartz crystal 630 at the back side 610B of the dual SPR/QCM sample holder 610.

The electrode 630 and the electrode 640 are attached to opposite sides of the quartz crystal 630. These two electrodes are for electric signals to make the quartz mechanically vibrate at 10 MHz. A reference electrode wire 631 through a reference electrode 632 and out of a top side 610C of the dual SPR/QCM sample holder 610. A counter electrode wire 614 passes from the sample chamber 618, through a reference electrode hole 642 and out of a top side 610C of the dual SPR/QCM sample holder 610. The reference electrode, counter electrode and working electrode can be used for integration of SPR and/or QCM with electrochemical experiments.

This dual SPR/QCM sample holder 610 design allows multi-techniques format (Electrochemistry, SPR and QCM) to be integrated to obtain additional information to under-stand and determine the binding events between the analyte in the solution and the surface receptors immobilized on the SPR and/or QCM gold surfaces. It also allows the generation of analyte of interest by electrochemistry and to determine whether the analyte of interest is present in the fluid sample by electrochemistry Quartz crystal Microbalance or electrochemistry Surface Plasmon Resonance technique.

EXAMPLES

Figure 15:
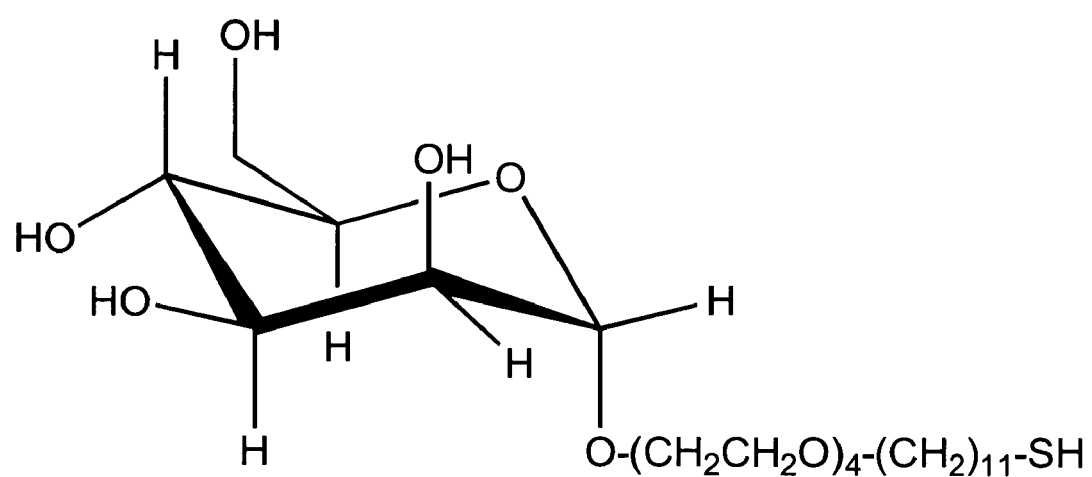
FIG. 15 is the molecular formula of a synthesized lipid mannose-SH used as a capture reagent.
Figure 16:
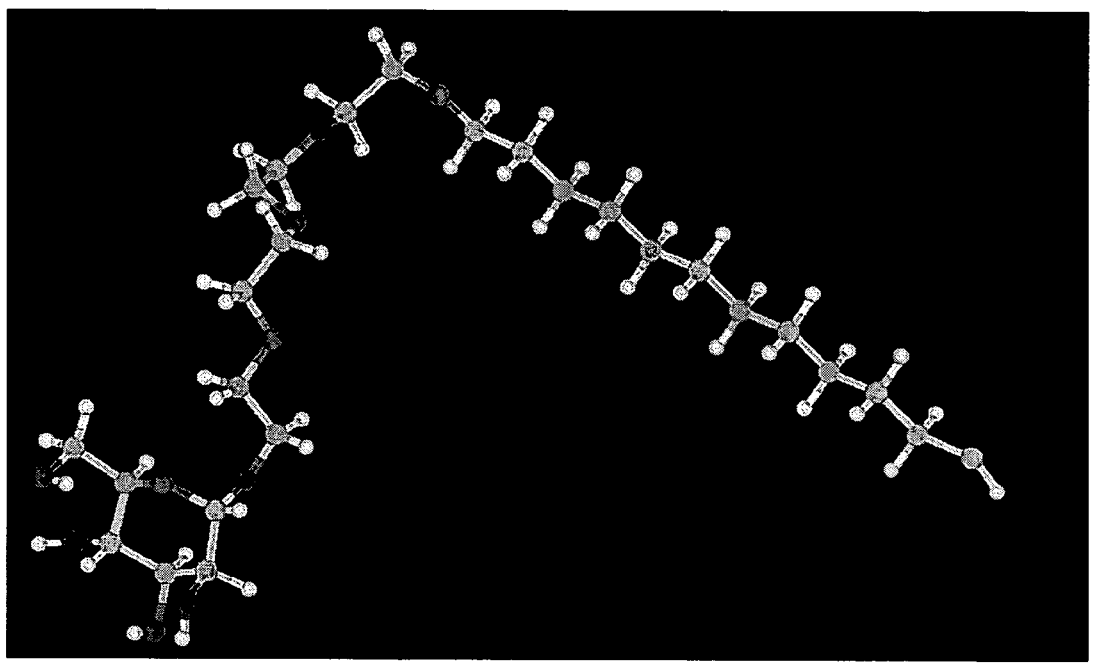
FIG. 16 is a three-dimensional model of the synthesized lipid mannose-SH molecule.
Figure 17A:
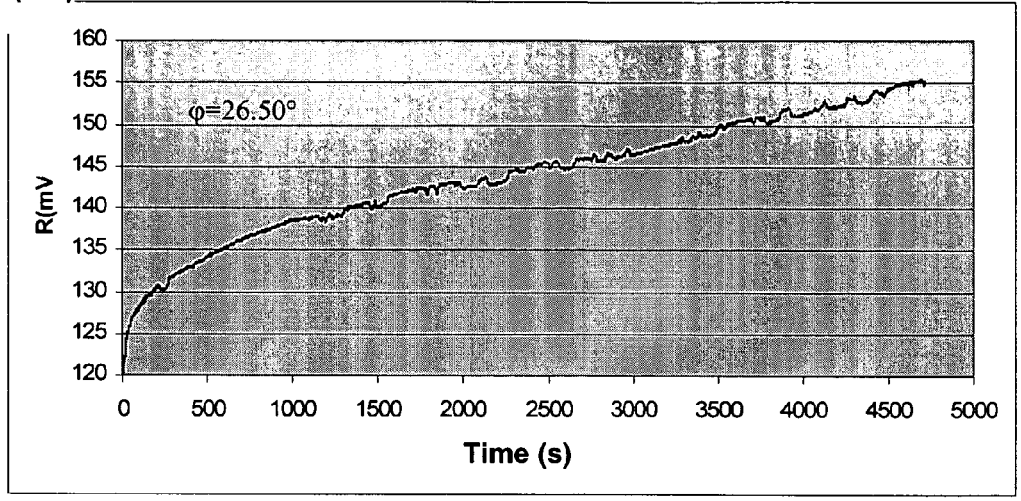
FIG. 17A is a graph illustrating mannose-SH lipid binding to a gold surface of the surface plasmon resonance biosensor 10 of FIG. 1 while the liquid in the chamber is ethanol. During measurements, the incident angle φ was fixed at 26.5°.
Figure 17B:
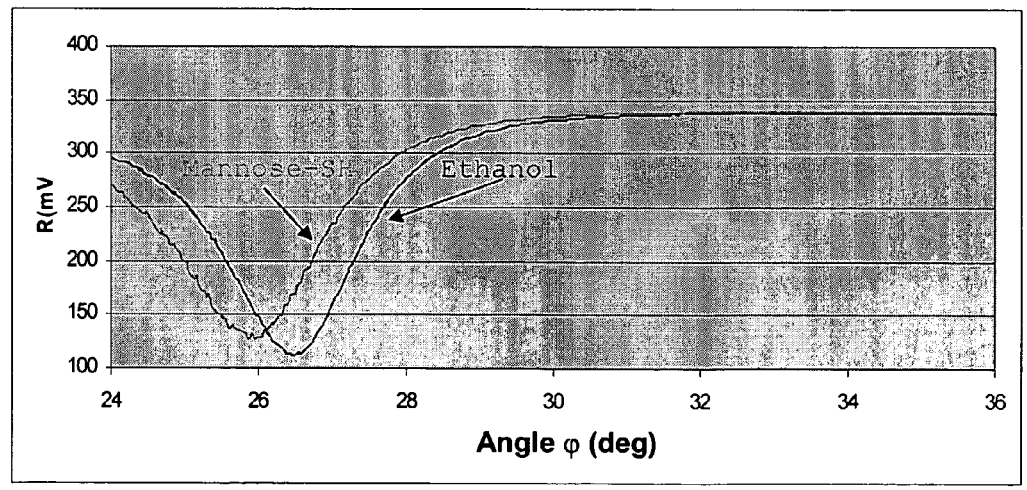
FIG. 17B is a graph showed the SPR spectra shift caused by Mannose-SH lipid in ethylnol.
Figure 18A:
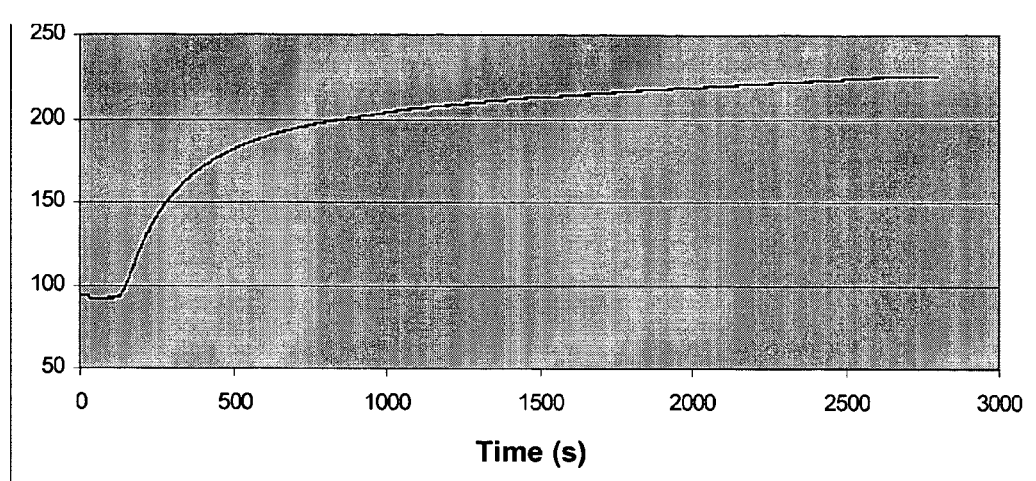
FIG. 18A and FIG. 18B are graphs illustrating protein Concanavalin A (Con A) in PBS buffer binding to the mannose-SH immobilized on the gold surface of the surface plasmon resonance biosensor 10 of FIG. 1. During measurements for FIG. 18A, the incident angle φ was fixed at 29.0°.
Figure 18B:
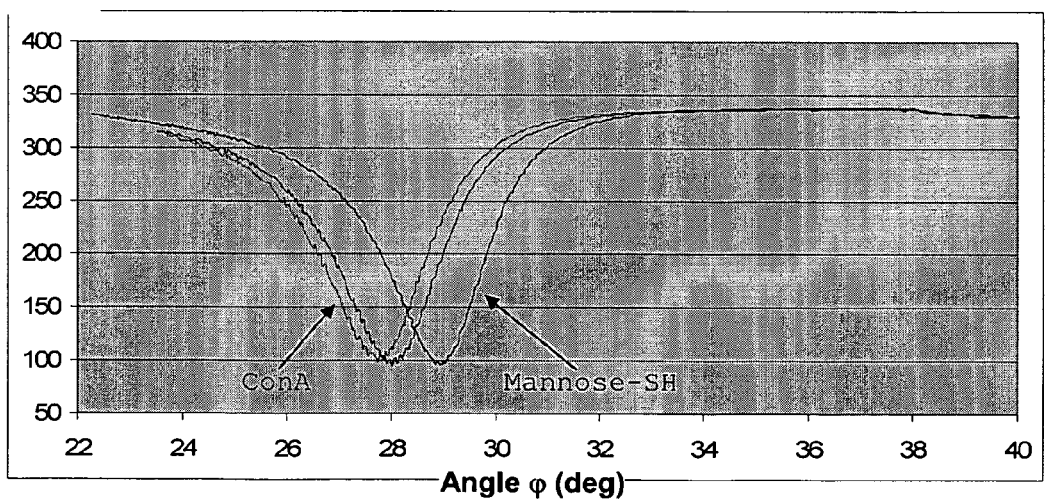
Figure 19A:
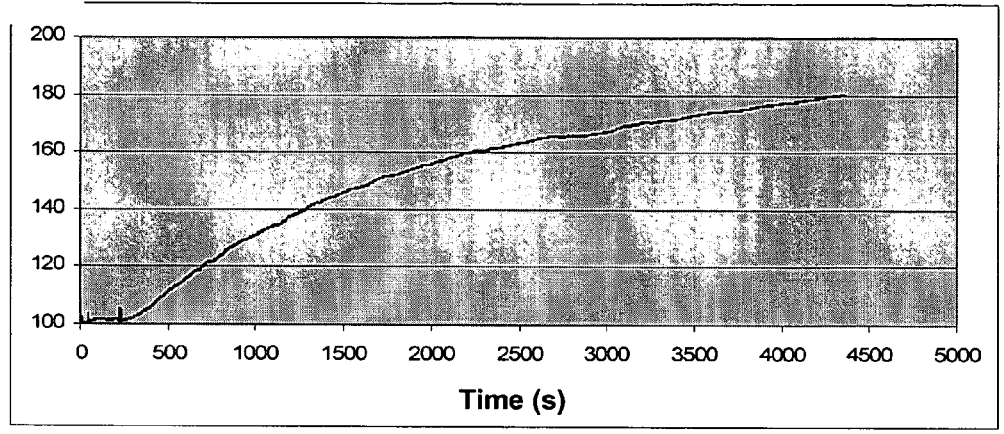
FIG. 19A and FIG. 19B are graphs illustrating *E. coli* K12 binding to the Con A surface (immobilized on the mannose-SH lipid monolyer on the gold surface of the surface plasmon resonance biosensor 10 of FIG. 1) if there are ConA molecules in the liquid. During measurements for FIG. 19A, the incident angle φ was fixed at 28.0°.
Figure 19B:
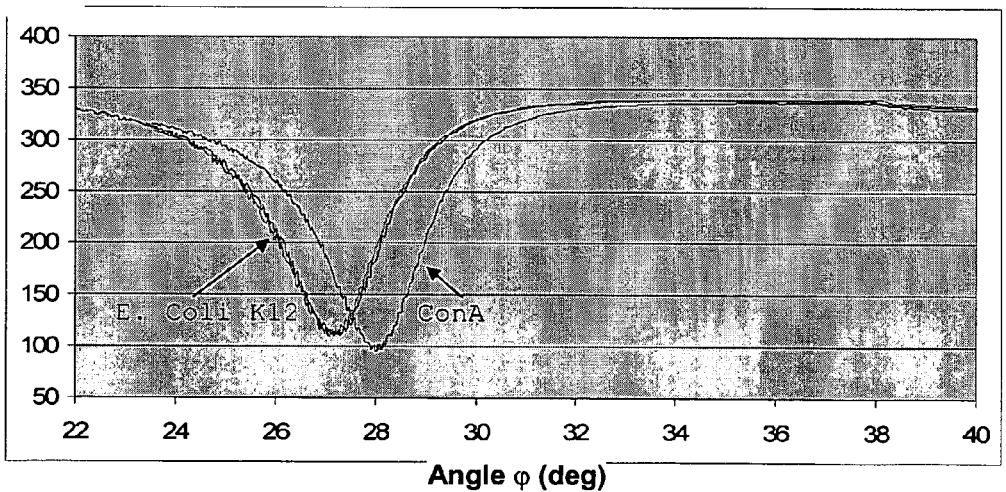

The portable SPR biosensor device (10, 110) of described in FIG. 1-FIG. 3 was used to detect *E. coli* K12 with a bound lipid mannose-SH sample layer 66 on the gold metallic film 60. FIG. 15 illustrates the molecular formula of the mannose-SH as a capture reagent bound to gold (Au) thin metallic film 60 of the surface plasmon resonance biosensor device 10 described above. The mannose-SH molecule has a formula of $C_{25}H_{50}O_{10}S$ and a molecular weight (Mr.) of 542.31. A three-dimensional model of the mannose-SH is illustrated in FIG. 16. FIGS. 17A and B illustrate mannose-SH binding to the gold (Au) surface as the thin metallic film 60 of the surface plasmon resonance biosensor device 10, in ethanol. As illustrated in FIGS. 18A and B, the lectin concanavalin A (ConA) binds to the mannose-SH bound to the gold (Au) surface. *E. Coli* K12 can bind to the ConA surface if there is ConA in the liquid, as illustrated in FIGS. 19A and B.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. A surface plasmon resonance biosensor system for analysis of a fluid sample comprising:
    (a) a support means;
    (b) a capacitive angle sensor mounted to the support means having a shaft;
    (c) a rotatable adapter means rotatably mounted on the shaft;
    (d) a prism or a half cylinder mounted on the rotatable adapter means;
    (e) a light source mounted to the support means, positioned to project a beam of light through a first side of the prism or half cylinder to a second side of the prism or half cylinder;
    (f) a thin metallic film with an inner surface affixed on or adjacent to the prism or half cylinder;
    (g) a sample holder having a sealing means removably sealed against an exposed surface of the thin metallic film, the sample holder, sealing means and thin metallic film defining a sample chamber;
    (h) a light response element as a transducer to generate an intensity output mounted on a third side of the prism or half cylinder, wherein when the sample is provided to the sample chamber and the light source projects the beam of light, the capacitive angle sensor measures an incident angle of the beam of light upon the metallic film to provide an incident angle output and the light response element measures light intensity reflected from the inner surface of the thin metallic film to provide the intensity output;
    (i) an analog to digital (A/D) data acquisition device electrically connected to the capacitive angle sensor and the light response element for generating a data signal when the sample is provided to the sample chamber from an incident angle output of the capacitive angle sensor and an intensity output from the light response element; and
    (j) a personal computer electrically connected to the data acquisition device to receive and process the data signal generated by the data acquisition device and provide a surface plasmon resonance spectrum when the fluid sample is provided to the sample chamber.

2. The surface plasmon resonance biosensor system of claim 1, wherein the metallic film is gold.

3. The surface plasmon resonance biosensor system of claim 1, wherein (i) the metallic film is gold and (ii) the metallic film comprises a capture reagent bound to a surface of the metallic film that is internal to the sample chamber.

4. The surface plasmon resonance biosensor system of claim 1, wherein the prism or half cylinder is made of glass or plastic.

5. The surface plasmon resonance biosensor system of claim 1, wherein the light response element is a solar cell.

6. The surface plasmon resonance biosensor system of claim 1, wherein the light source is a laser apparatus.

7. The surface plasmon resonance biosensor system of claim 1, wherein the rotatable adapter means is a rotatable plate.

8. The surface plasmon resonance biosensor system of claim 1, wherein the sealing means is an o-ring.

9. The surface plasmon resonance biosensor system of claim 1, wherein the support means is a mounting table.

10. The surface plasmon resonance biosensor system of claim 1, further comprising a low speed motor rotatably engaged with the rotatable adapter means to turn the rotatable adapter means during analysis of the sample.

11. The surface plasmon resonance biosensor system of claim 1, wherein the sample holder is a dual SPR/QCM sample holder which allows simultaneous detection by both surface plasmon resonance and also quartz crystal microbalance (QCM) techniques.

12. The surface plasmon resonance biosensor system of claim 1, comprising the prism mounted on the rotatable adapter means.

13. The surface plasmon resonance biosensor system of claim 1, wherein (i) the capacitive angle sensor measures an outside angle between the beam of light and the prism or half cylinder and (ii) the outside angle is correlated to the incident angle of the beam of light upon the metallic film to provide the incident angle output.

14. The surface plasmon resonance biosensor system of claim 11, wherein the dual SPR/QCM sample holder comprises (i) a first QCM electrode on a quartz crystal surface of the sample holder that is internal to the sample chamber and that opposes the thin metallic film, and (ii) a second QCM electrode on a quartz crystal surface of the sample holder that is external to the sample chamber and that opposes the first QCM electrode.

15. The surface plasmon resonance biosensor system of claim 1, wherein: (i) the thin metallic film serves as a working electrode; (ii) the sample chamber optionally comprises a counter electrode, a reference electrode, or both therein; and (iii) the sample chamber comprising the electrode or electrodes allows performance of electrochemistry techniques in the sample chamber.

16. The surface plasmon resonance biosensor system of claim 11, wherein: (i) the thin metallic film serves as a working electrode; (ii) the sample chamber comprises a counter electrode and a reference electrode therein; and (iii) the sample chamber comprising the electrodes allows performance of electrochemistry techniques in the sample chamber.

17. A surface plasmon resonance biosensor system for analysis of a fluid sample, the biosensor system comprising:
(a) a support table;
(b) a capacitive angle sensor mounted to the support table, the capacitive angle sensor having a shaft;
(c) a rotatable plate rotatably mounted on the shaft;
(d) a prism mounted on the rotatable plate;
(e) a light source mounted to the support table, positioned to project a beam of light through a first side of the prism to a second side of the prism;
(f) a thin gold metallic film with an inner surface affixed on or adjacent to the prism;
(g) a sample holder having a sealing means removably sealed against an exposed surface of the thin gold metallic film, wherein the sample holder, the sealing means and the thin gold metallic film define a sample chamber;
(h) a light response element as a transducer to generate an intensity output mounted on a third side of the prism, wherein when a sample is provided to the sample chamber and the light source projects the beam of light, the capacitive angle sensor measures an incident angle of the beam of light upon the gold metallic film to provide an incident angle output and the light response element measures light intensity reflected from the inner surface of the thin gold metallic film to provide the intensity output;
(i) an analog to digital (A/D) data acquisition device electrically connected to the capacitive angle sensor and the light response element for generating a data signal when the sample is provided to the sample chamber from an incident angle output of the capacitive angle sensor and an intensity output from the light response element; and
(j) a personal computer electrically connected to the data acquisition device to receive and process the data signal generated by the data acquisition device and provide a surface plasmon resonance spectrum when the fluid sample is provided to the sample chamber.

18. The surface plasmon resonance biosensor system of claim 17, wherein (i) the capacitive angle sensor measures an outside angle between the beam of light and the prism and (ii) the outside angle is correlated to the incident angle of the beam of light upon the metallic film to provide the incident angle output.

19. The surface plasmon resonance biosensor system of claim 18, wherein the sample holder is a dual SPR/QCM sample holder which allows simultaneous detection by both surface plasmon resonance and also quartz crystal microbalance (QCM) techniques, the dual SPR/QCM sample holder comprising: (i) a first QCM electrode on a quartz crystal surface of the sample holder that is internal to the sample chamber and that opposes the thin gold metallic film, and (ii) a second QCM electrode on a quartz crystal surface of the sample holder that is external to the sample chamber and that opposes the first QCM electrode.

20. The surface plasmon resonance biosensor system of claim 17, wherein: (i) the thin gold metallic film serves as a working electrode; (ii) the sample chamber optionally comprises a counter electrode, a reference electrode, or both therein; and (iii) the sample chamber comprising the electrode or electrodes allows performance of electrochemistry techniques in the sample chamber.

21. A surface plasmon resonance biosensor system for analysis of a fluid sample comprising:
(a) a support means;
(b) a capacitive angle sensor mounted to the support means having a shaft;
(c) a rotatable adapter means rotatably mounted on the shaft;
(d) a prism or a half cylinder mounted on the rotatable adapter means;
(e) a light source mounted to the support means, positioned to project a beam of light through a first side of the prism or half cylinder to a second side of the prism or half cylinder;
(f) a thin metallic film with an inner surface affixed on or adjacent to the prism or half cylinder;
(g) a sample holder having a sealing means removably sealed against an exposed surface of the thin metallic film, the sample holder, sealing means and thin metallic film defining a sample chamber;
(h) a light response element as a transducer to generate an intensity output adjacent to a third side of the prism or half cylinder, wherein when the sample is provided to the sample chamber and the light source projects the beam of light, the capacitive angle sensor measures an incident angle of the beam of light upon the metallic film to provide an incident angle output and the light response element measures light intensity reflected from the inner surface of the thin metallic film to provide the intensity output;
(i) an analog to digital (A/D) data acquisition device electrically connected to the capacitive angle sensor and the light response element for generating a data signal when the sample is provided to the sample chamber from an incident angle output of the capacitive angle sensor and an intensity output from the light response element; and
(j) a personal computer electrically connected to the data acquisition device to receive and process the data signal generated by the data acquisition device and provide a surface plasmon resonance spectrum when the fluid sample is provided to the sample chamber.

22. The surface plasmon resonance biosensor system of claim 21, wherein the light response element is a solar cell.

23. The surface plasmon resonance biosensor system of claim 21, wherein the sample holder is a dual SPR/QCM sample holder which allows simultaneous detection by both surface plasmon resonance and also quartz crystal microbalance (QCM) techniques.

24. The surface plasmon resonance biosensor system of claim 21, wherein an optical path between the light response element and the third side of the prism or half cylinder is free from an intervening lens.

* * * * *

UNITED STATES PATENT AND TRADEMARK OFFICE
CERTIFICATE OF CORRECTION

PATENT NO. : 7,943,092 B2  Page 1 of 1
APPLICATION NO. : 11/581260
DATED : May 17, 2011
INVENTOR(S) : Caide Xiao and Xiangqun Zeng It is certified that error appears in the above-identified patent and that said Letters Patent is hereby corrected as shown below:

Column 5, line 40, "is a graph showed" should be --is a graph showing--.

Column 7, line 49, "top view" should be --top view of--.

Column 9, line 19, "direct contacted" should be --direct contact--.

Column 9, line 29, "($\theta_{SRP}$)" should be --($\theta_{SPR}$)--.

Column 10, line 56, "a white-loop" should be --a while-loop--.

Column 10, line 59, "A white-loop" should be --a while-loop--.

Column 12, line 1, "also selective" should be --also selectively--.

Column 13, line 11, "of" should be deleted.

Signed and Sealed this
Third Day of January, 2012

David J. Kappos
*Director of the United States Patent and Trademark Office*